United States Patent
Weiss et al.

(10) Patent No.: US 6,207,392 B1
(45) Date of Patent: *Mar. 27, 2001

(54) SEMICONDUCTOR NANOCRYSTAL PROBES FOR BIOLOGICAL APPLICATIONS AND PROCESS FOR MAKING AND USING SUCH PROBES

(75) Inventors: Shimon Weiss, Pinole; Marcel Bruchez, Albany; Paul Alivisatos, Oakland, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/259,982

(22) Filed: Mar. 1, 1999

Related U.S. Application Data

(63) Continuation-in-part of application No. 08/978,450, filed on Nov. 25, 1997, now Pat. No. 5,990,479.

(51) Int. Cl.$^7$ ................................. G01J 5/02; G01J 3/30; F21V 4/16; H01J 65/06; C09K 11/06

(52) U.S. Cl. ................... 435/7.1; 250/352; 250/459.1; 356/317; 422/82.08; 252/301.17; 378/47; 436/546; 436/6

(58) Field of Search ................................. 250/307, 459.1, 250/302; 356/317; 422/82.08; 252/301.17; 378/47; 436/546; 435/6, 7.1

(56) References Cited

U.S. PATENT DOCUMENTS

| | | | |
|---|---|---|---|
| 3,996,345 | 12/1976 | Ullman et al. | 424/12 |
| 4,637,988 | 1/1987 | Hinshaw et al. | 436/546 |
| 4,777,128 | 10/1988 | Lippa | 435/5 |
| 5,262,357 | 11/1993 | Alivisatos et al. | . |
| 5,319,209 | 6/1994 | Miyakawa et al. | 250/459.1 |
| 5,505,928 | 4/1996 | Alivisatos et al. | . |
| 5,537,000 * | 7/1996 | Alivisatos et al. | 313/506 |
| 5,585,640 | 12/1996 | Huston et al. | 250/483.1 |
| 5,674,698 | 10/1997 | Zarling et al. | 435/7.92 |
| 5,736,330 | 4/1998 | Fulton | 435/6 |
| 5,751,018 | 5/1998 | Alivisatos et al. | . |
| 5,990,479 * | 11/1999 | Weiss et al. | 250/307 |

FOREIGN PATENT DOCUMENTS

| | | | |
|---|---|---|---|
| 0 990 903 | 4/2000 | (EP) | G01N/33/58 |
| WO 98/04740 | 2/1998 | (WO) | C12Q/1/68 |
| WO 99/19515 | 4/1999 | (WO) | C12Q/1/68 |

OTHER PUBLICATIONS

Lacoste, T.D., et al., "Super Resolution Molecular Ruler Using Single Quantum Dots", *Biophysical Journal*, vol. 78, Jan. 2000, p. 402A, XP–000933548 Abstract.

Alivisatos, A. P., "Semiconductor Clusters, Nanocrystals, and Quantum Dots," *Science* 271 (Feb. 16, 1996) :933–937.

Alivisatos, A. P., "Perspectives on the Physical Chemistry of Semiconductor Nanocrystals," *J. Phys. Chem.* 100 (1996) :13226–13239.

Alivisatos, A. Paul, et al., "Organization of 'Nanocrystal Molecules' Using DNA," *Nature* 382 (Aug. 15, 1996) :609–611.

Beverloo, H.B., et al., "Preparation and Microscopic Visualization of Multicolor Luminescent Immunophosphors," Chapter 4 of Beverloo, H.B., "Inorganic Crystals as Luminescent Labels: Their Applications in Immunocytochemistry and Time–Resolved Microscopy," Ph.D. dissertation, University of Leiden (The Netherlands), May 13, 1992, pp. 553–573.

Bruchez, Marcel P., Jr., "Luminescent Semiconductor Nanocrystals: Intermittent Behavior and Use as Fluorescent Biological Probes," Ph.D. dissertation, Universtiy of California, Dec. 17, 1998.

(List continued on next page.)

*Primary Examiner*—John S. Brusca
*Assistant Examiner*—Stephen Siu
(74) *Attorney, Agent, or Firm*—Paul R. Martin; Kerry S. Taylor; John F. Taylor

(57) ABSTRACT

A semiconductor nanocrystal compound is described which is capable of linking to one or more affinity molecules. The compound comprises (1) one or more semiconductor nanocrystals capable of, in response to exposure to a first energy, providing a second energy, and (2) one or more linking agents, having a first portion linked to the one or more semiconductor nanocrystals and a second portion capable of linking to one or more affinity molecules. One or more of these semiconductor nanocrystal compounds are linked to one or more affinity molecules to form a semiconductor nanocrystal probe capable of bonding with one or more detectable substances in a material being analyzed, and capable of, in response to exposure to a first energy, providing a second energy.

Treatment of a material with the semiconductor nanocrystal probe, and subsequent exposure of this treated material to a first energy, to determine the presence of the detectable substance within the material bonded to the probe, will excite the semiconductor nanocrystal in the probe bonded to the detectable substance, causing the probe to provide a second energy signifying the presence, in the material, of the detectable substance bonded to the semiconductor nanocrystal probe.

Also described are processes for respectively making the semiconductor nanocrystal compound and the semiconductor nanocrystal probe. Processes are also described for treating materials with the probe, for example, to determine the presence of a detectable substance in the material bonded to the probe.

155 Claims, 4 Drawing Sheets

OTHER PUBLICATIONS

Bruchez, Marcel, Jr. et al., "Semiconductor Nanocrystals as Fluorescent Probes for Biology", *Cytometry Supp.* 9 (1998) :26.

Chan, Warren C.W., et al., "Quantum Dot Bioconjugates for Ultrasensitive Nonisotopic Detection," *Science* 281 (Sep. 25, 1998) :2016–2018.

Coffer, Jeffrey L., et al., "Characterization of Quantum–Confined CdS Nanocrystallites Stablized by Deoxyribonucleic Acid (DNA)," *Nanotechnol.* 3 (1992) :69–76.

Cook, Neil D., "Scintillation Proximity Assay: A Versatile High–Throughput Screening Technology," *Drug Discovery Today* 1 (Jul. 1996) :287–294.

Correa–Duarte, Miguel A., et al., "Stabilization of CdS Semiconductor Nanoparticles Against Photodegradation by a Silica Coating Procedure," *Chem. Phys. Lett.* 286 (Apr. 17, 1998) :497–501.

Jacoby, Mitch, "Quantum Dots Meet Biomolecules," *C&E News* 76 (Sep. 28, 1998) :Copied from the Internet as pp. 1–3.

Kagan, C.R., et al, "Electronic Energy Transfer in CdSe Quantum Dot Solids," *Phys. Rev. Lett.* 76 (Feb. 26, 1996) :1517–1520.

Leff, David N., "Color–Coding Quantum Dots Debut with Promising Careers in Clinical Diagnostics Field," *Bioworld Today*, Sep. 25, 1998, Copied from the Internet as pp. 1–2.

Liz–Marzán, Luis M., et al., "Synthesis of Nanosized Gold–Silica Core–Shell Particles," *Langmuir* 12 (1996) :4329–4335.

Mahtab, Rahina, et al., "Preferential Adsorption of a 'Kinked' DNA to a Neutral Curved Surface: Comparisons to and Implications for Nonspecific DNA–Protein Interactions," *J. Am. Chem. Soc.* 118 (1996) :7028–7032.

Mahtab, Rahina, et al., "Protein–Sized Quantum Dot Luminescence Can Distinguish Between 'Straight,' 'Bent,' and 'Kinked' Oligonucleotides," *J. Am. Chem. Soc.* 117 bx;1(1995) :9099–9100.

Murphy, Catherine J., et al., "Quantum Dots as Inorganic DNA–Binding Proteins," *Mat. Res. Soc. Symp. Proc.* 452 (1997) :597–600.

Peng, Xiaogang, et al., "Synthesis and Isolation of a Homodimer of Cadmium Selenide Nanocrystals," *Angewandte Chemie–International Edition in English*, 36 (1997) :145–147.

Service, Robert F., "Semiconductor Beacons Light Up Cell Structures," *Science* 281 (Sep. 25, 1998) :1930–1931.

Shröck, E., et al., "Multicolor Spectral Karyotyping of Human Chromosomes," *Science* 273 (Jul. 26, 1996) :494–497.

Zhang, Yu–zhong, et al., "Novel Flow Cytometry Compensation Standards: Internally Stained Fluorescent Microspheres with Matched Emission Spectra and Long–Term Stability," *Cytometry* 33 (1998) :244–248.

Bruchez, Marcel, Jr., et al., "Semiconductor Nanocrystals as Fluorescent Biological Labels", *Science*, vol. 281, Sep. 25, 1998, pp. 2013–2016.

Dabbousi, B.O., et al., "(CdSe) ZnS Core–Shell Quantum Dots: Synthesis and Characterization of a Size Series of Highly Luminescent Nanocrystal–lites", *Journal of Physical Chemistry B*, vol. 101, 1997, pp. 9463–9475.

Peng, Xiaogang, et al., "Epitaxial Growth of Highly Luminescent CdSe/CdS Core/Shell Nanocrystals with Photostability and Electronic Accessibility", *Journal of the American Chemical Society*, vol. 119, No. 30, pp. 7019–7029.

* cited by examiner

SEMICONDUCTOR NANOCRYSTAL PROBES FOR BIOLOGICAL APPLICATIONS AND PROCESS FOR MAKING AND USING SUCH PROBES

CROSS-REFERENCE TO RELATED APPLICATION

This application is a continuation in part U.S. patent application Ser. No. 08/978,450 filed Nov. 25, 1997, now U.S. Pat. No. 5,990,047, assigned to the assignee of this application.

BACKGROUND OF THE INVENTION

The invention described herein arose in the course of, or under, Contract No. DE-AC03-SF00098 between the United States Department of Energy and the University of California for the operation of the Ernest Orlando Lawrence Berkeley National Laboratory. The Government may have rights to the invention.

1. Field of the Invention

This invention relates to semiconductor nanocrystal probes for biological applications wherein the probes include a plurality of semiconductor nanocrystals capable of providing a detectable signal in response to exposure to energy.

2. Description of the Related Art

Fluorescent labeling of biological systems is a well known analytical tool used in modern biotechnology as well as analytical chemistry. Applications for such fluorescent labeling include technologies such as medical (and non-medical) fluorescence microscopy, histology, flow cytometry, fluorescence in-situ hybridization (medical assays and research), DNA sequencing, immuno-assays, binding assays, separation, etc.

Conventionally, such fluorescent labeling involves the use of an organic dye molecule bonded to a moiety which, in turn, selectively bonds to a particular biological system, the presence of which is then identified by excitation of the dye molecule to cause it to fluoresce. There are a number of problems with such an analytical system. In the first place, the emission of light of visible wavelengths from an excited dye molecule usually is characterized by the presence of a broad emission spectrum as well as a broad tail of emissions on the red side of the spectrum, i.e., the entire emission spectrum is rather broad. As a result, there is a severe limitation on the number of different color organic dye molecules which may be utilized simultaneously or sequentially in an analysis since it is difficult to either simultaneously or even non-simultaneously detect or discriminate between the presence of a number of different detectable substances due to the broad spectrum emissions and emission tails of the labeling molecules. Another problem is that most dye molecules have a relatively narrow absorption spectrum, thus requiring either multiple excitation beams used either in tandem or sequentially for multiple wavelength probes, or else a broad spectrum excitation source which is sequentially used with different filters for sequential excitation of a series of probes respectively excited at different wavelengths.

Another problem frequently encountered with existing dye molecule labels is that of photostability. Available fluorescent molecules bleach, or irreversibly cease to emit light, under repeated excitation ($10^4$–$10^8$ cycles of absorption/emission). These problems are often surmounted by minimizing the amount of time that the sample is exposed to light, and by removing oxygen and/or other radical species from the sample.

In addition, the probe tools used for the study of systems by electron microscopy techniques are completely different from the probes used for study by fluorescence. Thus, it is not possible to label a material with a single type of probe for both electron microscopy and for fluorescence.

It would, therefore, be desirable to provide a stable probe material for biological applications preferably having a wide absorption band and capable of providing a detectable signal in response to exposure to energy, without the presence of the large red emission tails characteristic of dye molecules (thereby permitting the simultaneous use of a number of such probe materials, each, for example, emitting light of a different narrow wavelength band) and/or capable of scattering or diffracting radiation. It would also be equally desirable to provide a single, stable probe material which can be used to image the same sample by both light and electron microscopy.

SUMMARY OF THE INVENTION

The invention comprises a semiconductor nanocrystal compound capable of linking to one or more affinity molecules to form a semiconductor nanocrystal probe. The semiconductor nanocrystal compound comprises one or more semiconductor nanocrystals and one or more first linking agents. The one or more semiconductor nanocrystals are capable of providing a detectable signal in response to exposure to energy, wherein such a response may include emission and/or absorption and/or scattering or diffraction of the energy to which the one or more semiconductor nanocrystals are exposed. In addition to or as an alternative to providing a detectable signal, the one or more semiconductor nanocrystals may transfer energy to one or more proximal structures in response to exposure to energy. The one or more first linking agents have a first portion linked to one or more semiconductor nanocrystals and a second portion capable of lining either to one or more second linking agents or to one or more affinity molecules.

The invention further comprises a semiconductor nanocrystal probe formed either by (1) linking one or more of the above described semiconductor nanocrystal compounds to one or more affinity molecules; or (2) linking one or more of the above described semiconductor nanocrystal compounds to one or more second liking agents and linking the one or more second linking agents to one or more affinity molecules, wherein the one or more affinity molecules are capable of bonding to one or more detectable substances in a material. As a result, the semiconductor nanocrystal probe, in one embodiment, is capable of absorbing energy from either a particle beam or an electromagnetic radiation source (of broad or narrow bandwidth), and is capable of emitting detectable electromagnetic radiation in a narrow wavelength band when so excited; while in another embodiment the amount of energy from either a particle beam or an electromagnetic radiation source (of broad or narrow bandwidth) which is absorbed, or scattered, or diffracted by the semiconductor nanocrystal probe, is detectable, i.e., the change in absorption, scattering, or diffraction is detectable. In yet another embodiment, the semiconductor nanocrystal probe is capable of receiving energy transferred from a proximal source and/or transferring energy to one or more proximal structures in response to exposure to energy.

The invention also comprises a process for making the semiconductor nanocrystal compound and for making the semiconductor nanocrystal probe comprising the semiconductor nanocrystal compound linked to one or more affinity molecules capable of bonding to one or more detectable substances. The semiconductor nanocrystal probe of the invention is stable with respect to repeated excitation by light, or exposure to elevated temperatures, or exposure to oxygen or other radicals.

The invention further comprises a process for treating a material, such as a biological material, to determine the presence of a detectable substance in the material, which comprises a step of contacting the material to be treated, with the semiconductor nanocrystal probe, an optional ID step of removing from the material the semiconductor nanocrystal probes not bonded to the detectable substance, and then a step of exposing the material to energy from, for example, either an electromagnetic radiation source (of broad or narrow bandwidth) or a particle beam. The presence of the detectable substance in the material is then determined by a step of detecting the signal provided by the semiconductor nanocrystal probe in response to exposure to energy. This may be accomplished, for example, either by measuring the absorption of energy by the semiconductor nanocrystal probe and/or detecting the emission of radiation of a narrow wavelength band by the semiconductor nanocrystal probe and/or detecting the scattering or diffraction of energy by the semiconductor nanocrystal probe, indicative (in either case) of the presence of the semiconductor nanocrystal probe bonded to the detectable substance in the material.

The invention further comprises a process for treating a material, such as a biological material with a semiconductor nanocrystal probe which is used to transfer energy to one or more proximal structures. This process comprises a step of contacting the material to be treated, with the semiconductor nanocrystal probe, an optional step of removing from the material portions of the semiconductor nanocrystal probe not bonded to the detectable substance, and then a step of exposing the material to energy from, for example, either an electromagnetic radiation source (of broad or narrow bandwidth) or a particle beam. This is followed by a step of energy transfer from the semiconductor nanocrystal probe to one or more proximal structures which may, in response to the energy transfer, either provide a detectable signal, undergo chemical or conformational changes, or transfer energy to one or more second proximal structures.

The use of the semiconductor nanocrystal probe in the treatment of a material to either provide a detectable signal or transfer energy to a proximal structure may be applied to a plurality of medical and non-medical biological applications. Exemplary applications of the semiconductor nanocrystal probe include: use as a detector of substances on the surface or interior of cells in flow cytometry; use in a plurality of methods for detecting nucleic acid sequences by hybridization, such as fluorescence in-situ hybridization (particularly when the semiconductor nanocrystal probe has been modified in a polymerase chain reaction); or use to transfer energy which may cause the release of a cytotoxic molecule or transfer of heat energy, either of which may result in death of specifically targeted cells. Another use of the semiconductor nanocrystal probe is as a precursor which is treated to synthetic steps which result in a modified semiconductor nanocrystal probe (as in the case of modification by polymerase chain reaction).

DETAILED DESCRIPTION OF THE INVENTION

Figure 1:
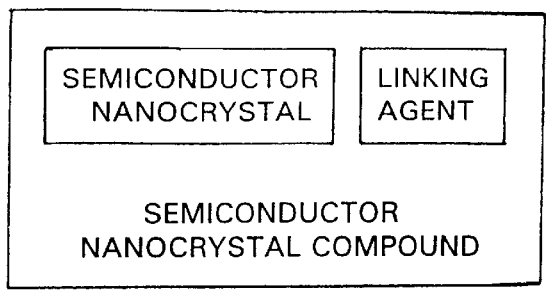
FIG. 1 is a block diagram of the semiconductor nanocrystal compound of the invention.
Figure 2:
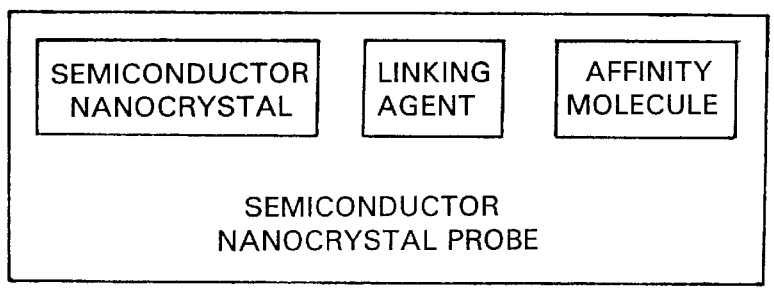
FIG. 2 is a block diagram of the semiconductor nanocrystal probe of the invention.
Figure 3:
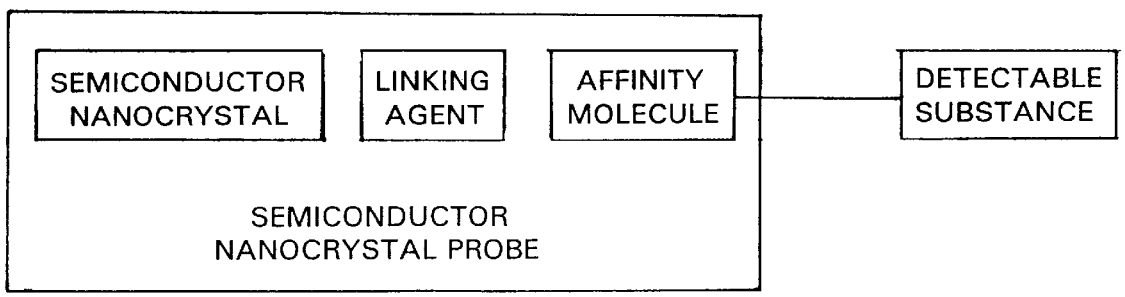
FIG. 3 is a block diagram showing the affinity between a detectable substance and the semiconductor nanocrystal probe of the invention.
Figure 4:
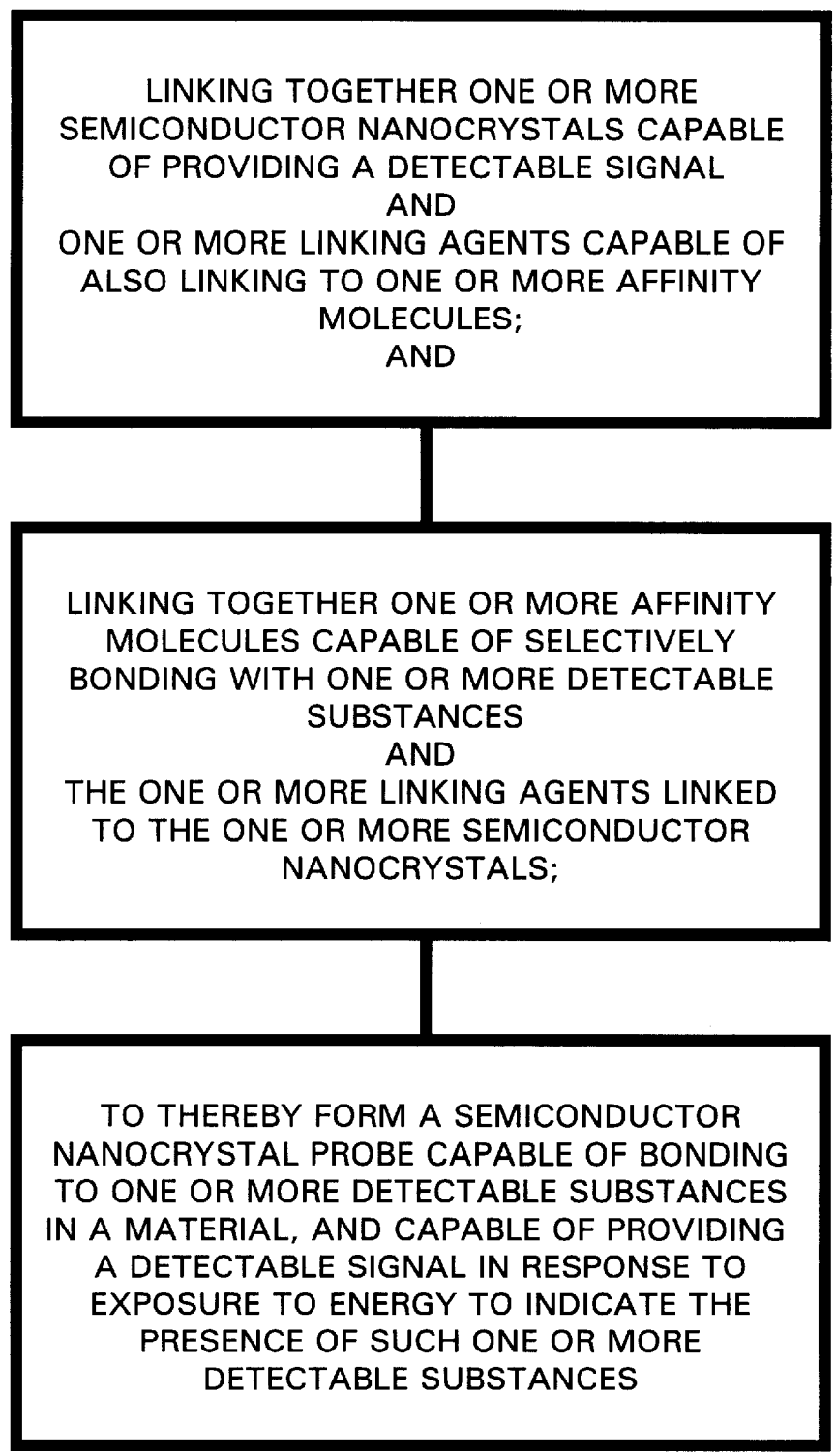
FIG. 4 is a flow sheet illustrating the process of forming the semiconductor nanocrystal probe of the invention.
Figure 5:
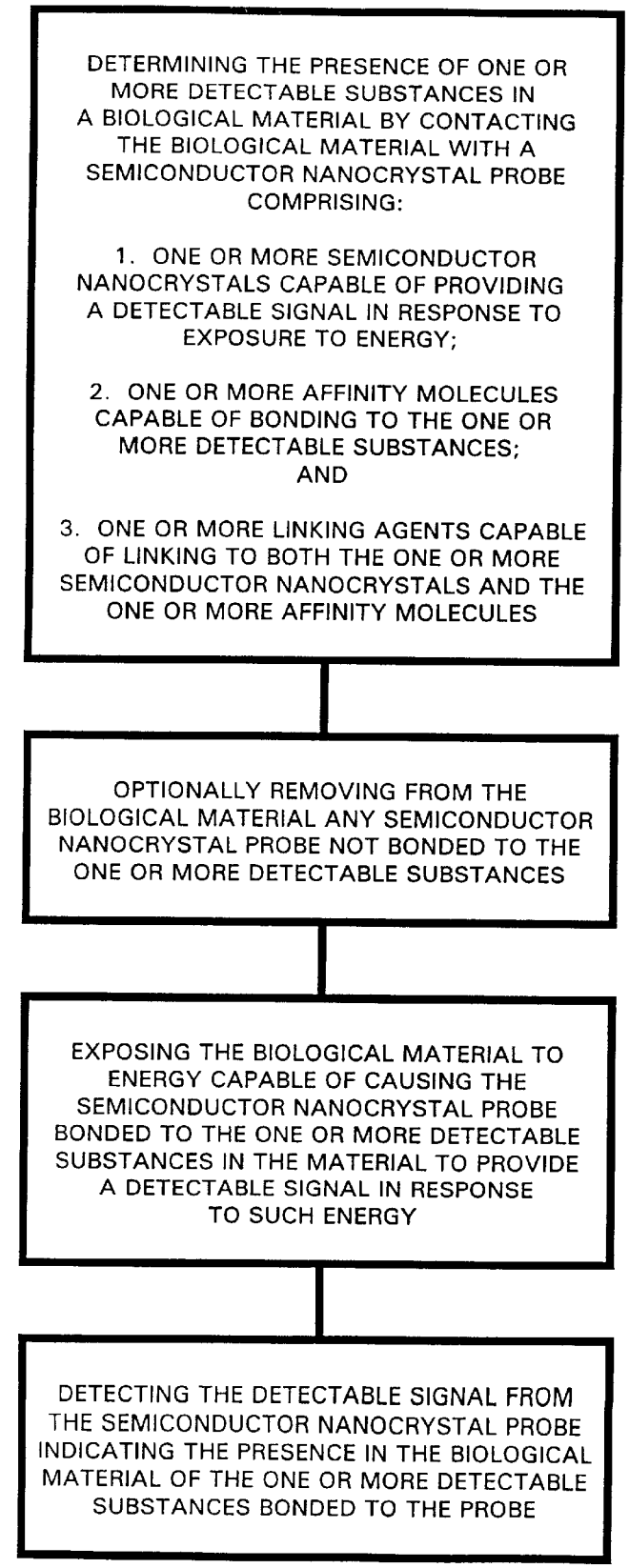
FIG. 5 is a flow sheet illustrating a typical use of the semiconductor nanocrystal probe of the invention in detecting the presence of a detectable substance in a material such as a biological material.
Figure 6:
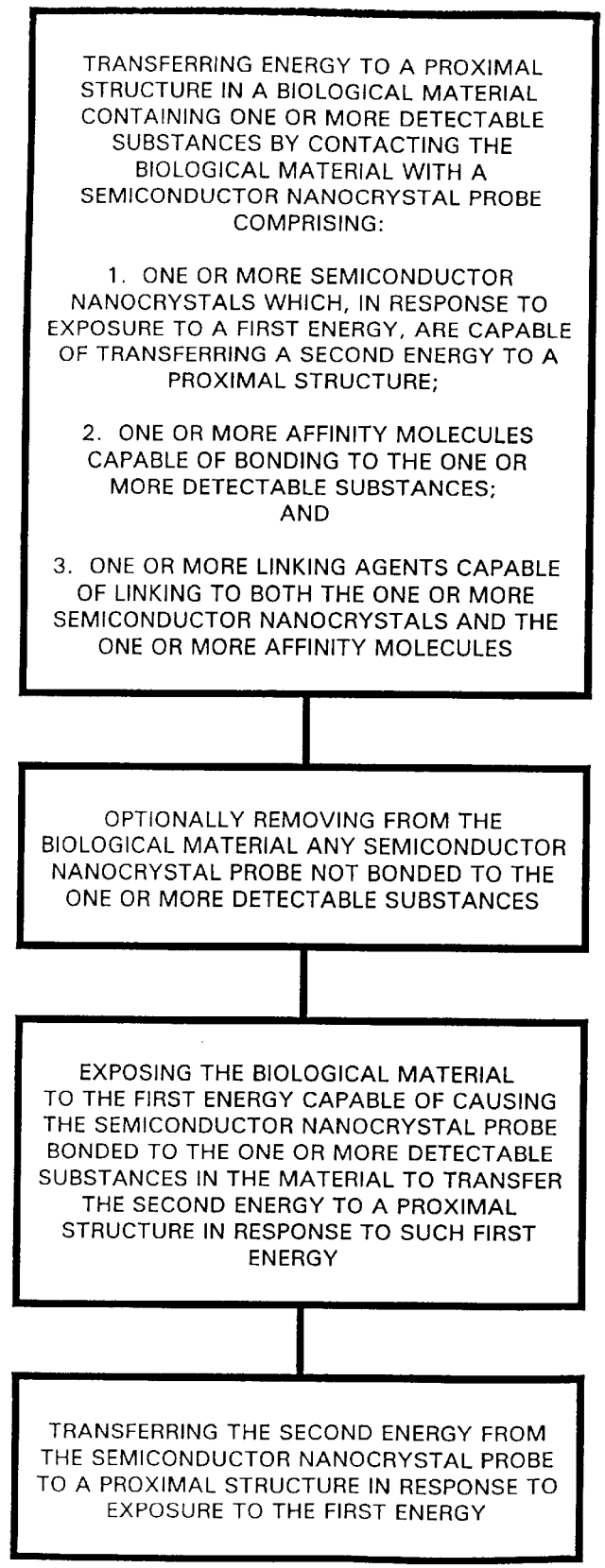
FIG. 6 is a flow sheet illustrating a typical use of the semiconductor nanocrystal probe of the invention in transferring energy to a proximal structure.

The invention comprises a semiconductor nanocrystal compound capable of linking to either one or more second linking agents or to one or more affinity molecules, and capable of providing a detectable signal in response to exposure to energy. The semiconductor nanocrystal compound, in turn, comprises: (1) one or more semiconductor nanocrystals, each capable of providing a detectable signal in response to exposure to energy; and (2) one or more first linking agents, each having a first portion linked to the semiconductor nanocrystal and a second portion capable of linking either to one or more second linking agents or to one or more affinity molecules.

The invention also comprises the above described semiconductor nanocrystal compound linked to one or more affinity molecules (through either one or more first linking agents, or through one or more second linking agents which are in turn linked to one or more first linking agents) to form a semiconductor nanocrystal probe capable of bonding to one or more detectable substances and capable of providing a detectable signal in response to exposure to energy. Treatment of a material (typically a biological material) with the semiconductor nanocrystal probe, and subsequent exposure of this treated material to energy, as described above, to determine the presence of the detectable substance within the material, will result in the semiconductor nanocrystal in the semiconductor nanocrystal probe bonded to the detectable substance providing a detectable signal. This detectable signal, such as a change in absorption and/or emission of electromagnetic radiation of a narrow wavelength band and/or scattering or diffraction may signify (in either instance) the presence in the material, of the detectable substance bonded to the semiconductor nanocrystal probe.

The invention also comprises a process for making the semiconductor nanocrystal compound, and a process for making the semiconductor nanocrystal probe comprising the semiconductor nanocrystal compound linked to one or more affinity molecules capable of bonding to one or more detectable substances.

The invention further comprises a process for treating a material, such as a biological material, to determine the presence of one or more detectable substances in the material which comprises: (1) contacting the material with the semiconductor nanocrystal probe, (2) (optionally) removing from the material the semiconductor nanocrystal probes not bonded to the detectable substance, (3) exposing the material to energy (such as the above-described electromagnetic energy source or particle beam), to which, the semiconductor nanocrystal is capable of providing a response, signifying the presence of the semiconductor nanocrystal probe bonded to the detectable substance in the material, and (4) detecting the signal provided by the semiconductor nanocrystal in the semiconductor nanocrystal probe.

The invention further comprises a process for treating a material, such as a biological material, using a semiconductor nanocrystal probe, which comprises: (1) contacting the material with the semiconductor nanocrystal probe, (2) (optionally) removing from the material the semiconductor nanocrystal probes not bonded to the detectable substance, (3) exposing the material to energy (such as an electromagnetic energy source or particle beam) capable of causing a transfer of energy from one or more semiconductor nanocrystal probes to one or more proximal structures in response to exposure to energy, and (4) transferring energy from one or more semiconductor nanocrystal probes to one or more proximal structures.

a. Definitions

By use of the terms "nanometer crystal" or "nanocrystal" herein is meant an organic or 20 inorganic crystal particle, preferably a single crystal particle, having an average cross-section no larger than about 20 nanometers (nm) or $20 \times 10^{-9}$ meters (200 Angstroms), preferably no larger than about 10 nm (100 Angstroms) and a minimum average cross-section of about 1 nm, although in some instances a smaller average cross-section nanocrystal, i.e., down to about 0.5 nm (5 Angstroms), may be acceptable. Typically the nanocrystal will have an average cross-section ranging in size from about 1 nm (10 Angstroms) to about 10 nm (100 angstroms).

By use of the term "semiconductor nanocrystal" is meant a nanometer crystal or nanocrystal of Group II-VI and/or Group III-V semiconductor compounds capable of emitting electromagnetic radiation upon excitation, although the use of Group IV semiconductors such as germanium or silicon, or the use of organic semiconductors, may be feasible under certain conditions.

The term "radiation," as used herein, is meant to include electromagnetic radiation, including x-ray, gamma, ultraviolet, visible, infra-red, and microwave radiation; and particle radiation, including electron beam, beta, and alpha particle radiation.

The term "energy" is intended to include electromagnetic radiation, particle radiation, and fluorescence resonance energy transfer (FRET). As used herein, the term "first energy" is meant the energy to which a semiconductor nanocrystal is exposed. Use of the term "second energy" is meant energy provided by a semiconductor nanocrystal, within a semiconductor nanocrystal compound or within a semiconductor nanocrystal probe, in response to exposure to a first energy. It should be noted that different nanocrystals, when exposed to the same "first energy", may respectively provide "second energies" which differ from one another, and the use of the term "second energy", when used in connection with a plurality of semiconductor nanocrystals will be understood to refer to either second energies which are the same or to a plurality of different second energies.

By the use of the term "energy transfer" is meant the transfer of energy from one atom or molecule to another atom or molecule by either radiative or non-radiative pathways.

The term "proximal source" is meant an atom, a molecule, or any other substance which is capable of transferring energy to and/or receiving energy transferred from another atom or molecule or any other substance.

The term "proximal structure" as used herein may be an atom, a molecule, or any other substance (e.g. a polymer, a gel, a lipid bilayer, and any substance bonded directly to a semiconductor nanocrystal probe) which is capable of receiving energy transferred from another atom or molecule or other substance (including a semiconductor nanocrystal probe). By use of the term "a narrow wavelength band", with regard to the electromagnetic radiation mission of the semiconductor nanocrystal, is meant a wavelength band of emissions not exceeding about 40 nm, and preferably not exceeding about 20 nm in width and symmetric about the center, in contrast to the emission bandwidth of about 100 nm for a typical dye molecule, with a red tail which may extend the band width out as much as another 100 nm. It should be noted that the bandwidths referred to are determined from measurement of the width of the emissions at half peak height (FW, and are appropriate in the range of 200 nm to 2000 nm.

By use of the term "a broad wavelength band", with regard to the electromagnetic radiation absorption of the semiconductor nanocrystal is meant absorption of radiation having a wavelength equal to, or shorter than, the wavelength of the onset radiation (the onset radiation is understood to be the longest wavelength (lowest energy) radiation capable of being absorbed by the semiconductor nanocrystal), which occurs near to, but at slightly higher energy than the "narrow wavelength band" of the emission. This is in contrast to the "narrow absorption band" of dye molecules which occurs near the emission peak on the high energy side, but drops off rapidly away from that wavelength and is often negligible at wavelengths further than 100 nm from the emission.

The term "detectable signal," as used herein, is meant to include emission by the semiconductor nanocrystal of electromagnetic radiation, including visible or infrared or ultraviolet light and thermal emission; and any other signal or change in signal emanating from the semiconductor nanocrystal evidencing scattering (including diffraction) and/or absorption in response to exposure of the semiconductor nanocrystal to radiation.

By use of the term "detectable substance" is meant an entity or group or class of groups, the presence or absence of which, in a material such as a biological material, is to be ascertained by use of the semiconductor nanocrystal probe of the invention.

By use of the term "affinity molecule" is meant the portion of the semiconductor nanocrystal probe of the invention which comprises an atom, molecule, or other moiety capable of selectively bonding to one or more detectable substances (if present) in the material (e.g., biological material) being analyzed.

The use of the term "small molecule" as used herein (for either an affinity molecule or a detectable substance) is any atom or molecule, inorganic or organic, including biomolecules, having a molecular weight below about 10,000 daltons (grams/mole).

By use of the term "linking agent" is meant a substance capable of linking with one or more semiconductor nanocrystals and also capable of linking to one or more affinity molecules or one or more second linking agents.

By use of the term "first linking agent" is meant a substance capable of either (1) linking with one or more semiconductor nanocrystals, and also capable of linking to one or more affinity molecules; or (2) linking with one or more semiconductor nanocrystals and also capable of lining to one or more second linking agents.

By use of the term "second linking agent" is meant a substance capable of linking to one or more affinity molecules and also capable of linking to one or more linking agents.

Use of the term "three-dimensional structure" herein is meant to define any structure, independent of shape, which is greater than 10 nm in thickness along the three mutually perpendicular principle axes of the structure.

Use of the term "substructure" herein is meant one of two or more portions of a three-dimensional structure.

The terms "link" and "linking" are meant to describe the adherence between the one or more affinity molecules and the one or more semiconductor nanocrystals, either directly or through one or more moieties identified herein as linking agents (including second linking agents between the linking agent and the affinity molecule). The adherence may comprise any sort of bond, including, but not limited to, covalent, ionic, hydrogen bonding, van der Waals forces, or mechanical bonding, etc.

The terms "bond" and "bonding" are meant to describe the adherence between the affinity molecule and the detectable substance. The adherence may comprise any sort of bond, including, but not limited to, covalent, ionic, or hydrogen bonding, van der Waals forces, or mechanical bonding, etc.

The term "semiconductor nanocrystal compound", as used herein, is intended to define one or more semiconductor nanocrystals linked to one or more first linking agents and capable of linking to either one or more second linking agents or to one or more affinity molecules, while the term "semiconductor nanocrystal probe" is intended to define a semiconductor nanocrystal compound linked to one or more affinity molecules.

The term "glass" as used herein is intended to include one or more oxides of silicon, boron, and/or phosphorus, or a mixture thereof, as well as the further optional inclusion of one or more metal silicates, metal borates or metal phosphates therein.

b. The Semiconductor Nanocrystals

The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. As mentioned above, the use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations of same.

Formation of nanometer crystals of Group III-V semiconductors is described in copending and commonly assigned Alivisatos et al. U.S. Pat. No. 5,571,018; Alivisatos et al. U.S. Pat. No. 5,505,928; and Alivisatos et al. U.S. Pat. No. 5,262,357, which also describes the formation of Group II-VI semiconductor nanocrystals, and which is also assigned to the assignee of this invention. Also described therein is the control of the size of the semiconductor nanocrystals during formation using crystal growth terminators. The teachings of Alivisatos et al. U.S. Pat. No. 5,571,018, and Alivisatos et al. U.S. Pat. No. 5,262,357 are each hereby specifically incorporated by reference.

In one embodiment, the nanocrystals are used in a core/shell configuration wherein a first semiconductor nanocrystal forms a core ranging in diameter, for example, from about 20 Å to about 100 Å, with a shell of another semiconductor nanocrystal material grown over the core nanocrystal to a thickness of, for example, 1–10 monolayers in thickness. When, for example, a 1–10 monolayer thick shell of CdS is epitaxially grown over a core of CdSe, there is a dramatic increase in the room temperature photoluminescence quantum yield. Formation of such core/shell nanocrystals is described more fully in a publication by one of us with others entitled "Epitaxial Growth of Highly Luminescent CdSe/CdS Core/Shell Nanocrystals with Photostability and Electronic Accessibility", by Peng, Schlamp, Kadavanich, and Alivisatos, published in the Journal of the American Chemical Society, Volume 119, No. 30. 1997, at pages 7019–7029, the subject matter of which is hereby specifically incorporated herein by reference.

The semiconductor nanocrystals used in the invention will have a capability of absorbing radiation over a broad wavelength band. This wavelength band includes the range from gamma radiation to microwave radiation. In addition, these semiconductor nanocrystals will have a capability of emitting radiation within a narrow wavelength band of about 40 nm or less, preferably about 20 nm or less, thus permitting the simultaneous use of a plurality of differently colored semiconductor nanocrystal probes with different semiconductor nanocrystals without overlap (or with a small amount of overlap) in wavelengths of emitted light when exposed to the same energy source. Both the absorption and emission properties of semiconductor nanocrystals may serve as advantages over dye molecules which have narrow wavelength bands of absorption (e.g. about 30–50 nm) and broad wavelength bands of emission (e.g. about 100 nm) and broad tails of emission (e.g. another 100 nm) on the red side of the spectrum. Both of these properties of dyes impair the ability to use a plurality of differently colored dyes when exposed to the same energy source.

Furthermore, the frequency or wavelength of the narrow wavelength band of light emitted from the semiconductor nanocrystal may be further selected according to the physical properties, such as size, of the semiconductor nanocrystal. The wavelength band of light emitted by the semiconductor nanocrystal, formed using the above embodiment, may be determined by either (1) the size of the core, or (2) the size of the core and the size of the shell, depending on the composition of the core and shell of the semiconductor nanocrystal. For example, a nanocrystal composed of a 3 nm core of CdSe and a 2 nm thick shell of CdS will emit a narrow wavelength band of light with a peak intensity wavelength of 600 nm. In contrast, a nanocrystal composed of a 3 nm core of CdSe and a 2 nm thick shell of ZnS will emit a narrow wavelength band of light with a peak intensity wavelength of 560 nm.

A plurality of alternatives to changing the size of the semiconductor nanocrystals in order to selectably manipulate the emission wavelength of semiconductor nanocrystals exist. These alternatives include: (1) varying the composition of the nanocrystal, and (2) adding a plurality of shells around the core of the nanocrystal in the form of concentric shells. It should be noted that different wavelengths can also be obtained in multiple shell type semiconductor nanocrystals by respectively using different semiconductor nanocrystals in different shells, i.e., by not using the same semiconductor nanocrystal in each of the plurality of concentric shells.

Selection of the emission wavelength by varying the composition, or alloy, of the semiconductor nanocrystal is old in the art. As an illustration, when a CdS semiconductor nanocrystal, having an emission wavelength of 400 nm, may be alloyed with a CdSe semiconductor nanocrystal, having an emission wavelength of 530 nm. When a nanocrystal is prepared using an alloy of CdS and CdSe, the wavelength of the emission from a plurality of identically sized nanocrystals may be tuned continuously from 400 nm to 530 nm depending on the ratio of S to Se present in the nanocrystal. The ability to select from different emission wavelengths while maintaining the same size of the semiconductor nanocrystal may be important in applications which require the semiconductor nanocrystals to be uniform in size, or for example, an application which requires all semiconductor nanocrystals to have very small dimensions when used in application with steric restrictions.

c.. Affinity Molecules

The particular affinity molecule forming a part of the semiconductor nanocrystal probe of the invention will be selected based on its affinity for the particular detectable substance whose presence or absence, for example, in a biological material, is to be ascertained. Basically, the affinity molecule may comprise any molecule capable of being linked to one or more semiconductor nanocrystal compounds which is also capable of specific recognition of a particular detectable substance. In general, any affinity molecule useful in the prior art in combination with a dye molecule to provide specific recognition of a detectable substance will find utility in the formation of the semiconductor nanocrystal probes of the invention. Such affinity molecules include, by way of example only, such classes of substances as monoclonal and polyclonal antibodies, nucleic acids (both monomeric and oligomeric), proteins, polysaccharides, and small molecules such as sugars, peptides, drugs, and ligands. Lists of such affinity molecules are available in the published literature such as, by way of example, the "Handbook of Fluorescent Probes and Research Chemicals", (sixth edition) by R. P. Haugland, available from Molecular Probes, Inc.

d. The Linking Agents

The semiconductor nanocrystal probe of the invention will usually find utility with respect to the detection of one or more detectable substances in organic materials, and in particular to the detection of one or more detectable substances in biological materials. This requires the presence, in the semiconductor nanocrystal probe, of an affinity molecule or moiety, as described above, which will bond the semiconductor nanocrystal probe to the detectable substance in the organic/biological material so that the presence of the detectable material may be subsequently ascertained. However, since the semiconductor nanocrystals are inorganic, they may not bond directly to the affinity molecule. In this case therefore, there must be some type of linking agent present in the semiconductor nanocrystal probe which is capable of liking the inorganic semiconductor nanocrystal to the affinity molecule in the semiconductor nanocrystal probe. The linking agent may be in the form of one or more linking agents linking one or more semiconductor nanocrystals to one or more affinity molecules. Alternatively, two types of linking agents may be utilized. One or more of the first linking agents may be linked to one or more semiconductor nanocrystals and also linked to one or more second linking agents. The one or more second linking agents may be linked to one or more affinity molecules and to one or more first linking agents.

One form in which the semiconductor nanocrystal may be linked to an affinity molecule via a linking agent is by coating the semiconductor nanocrystal with a thin layer of glass, such as silica ($SiO_x$ where x=1–2), using a linking agent such as a substituted silane, e.g., 3-mercaptopropyl-trimethoxy silane to in the nanocrystal to the glass. The glass-coated semiconductor nanocrystal may then be further treated with a linking agent, e.g., an amine such as 3-aminopropyl-trimethoxysilane, which will function to link the glass-coated semiconductor nanocrystal to the affinity molecule. That is, the glass-coated semiconductor nanocrystal may then be linked to the affinity molecule. It is within the contemplation of this invention that the original semiconductor nanocrystal compound may also be chemically modified after it has been made in order to link effectively to the affinity molecule. A variety of references summarize the standard classes of chemistry which may be used to this end, in particular the "Handbook of Fluorescent Probes and Research Chemicals", (6th edition) by R. P. Haugland, available from Molecular Probes, Inc., and the book "Bioconjugate Techniques", by Greg Hermanson, available from Academic Press, New York.

When the semiconductor nanocrystal may be coated with a thin layer of glass, the glass, by way of example, may comprise a silica glass ($SiO_x$ where x=1–2), having a thickness ranging from about 0.5 nm to about 10 nm, and preferably from about 0.5 nm to about 2 nm.

The semiconductor nanocrystal is coated with the coating of thin glass, such as silica, by first coating the nanocrystals with a surfactant such as tris-octyl-phosphine oxide, and then dissolving the surfactant-coated nanocrystals in a basic methanol solution of a linking agent, such as 3-mercaptopropyl-tri-methoxy silane, followed by partial hydrolysis which is followed by addition of a glass-affinity molecule linking agent such as amino-propyl trimethoxysilane which will link to the glass and serve to form a link with the affinity molecule.

When the linking agent does not involve the use of a glass coating on the semiconductor nanocrystal, it may comprise a number of different materials, depending upon the particular affinity molecule, which, in turn, depends upon the type of detectable material being analyzed for. It should also be noted that while an individual linking agent may be used to link to an individual semiconductor nanocrystal, it is also within the contemplation of the invention that more than one linking agent may bond to the same semiconductor nanocrystal and vice versa; or a plurality of linking agents may be used to link to a plurality of semiconductor nanocrystals. In addition, when first and second linking agents are used, one or more first linking agents may be linked to the same second linking agent, or more than one second linking agents may be linked to the same first linking agent.

A few examples of the types of linking agents which may be used to link to both the semiconductor nanocrystal (or to a glass coating on the nanocrystal) and to the affinity molecule in the probe are illustrated in the table below, it being understood that this is not intended to be an exhaustive list:

Linking Agent

| Structure | Name |
| --- | --- |
| HS—C$_6$H$_4$—C(=O)—NH—CH$_2$CH$_2$CH$_2$—NH$_2$ | N-(3-aminopropyl)3-mercapto-benzamide |
| (CH$_3$O)$_3$Si—CH$_2$CH$_2$CH$_2$—NH$_2$ | 3-aminopropyl-trimethoxysilane |
| (CH$_3$O)$_3$Si—CH$_2$CH$_2$CH$_2$—SH | 3-mercaptopropyl-trimethoxysilane |
| (CH$_3$O)$_3$Si—CH$_2$CH$_2$CH$_2$—N(maleimide) | 3-(trimethoxysilyl)propyl-maleimide |
| (CH$_3$O)$_3$Si—CH$_2$CH$_2$CH$_2$—C(=O)—NH—NH$_2$ | 3-(trimethoxysilyl)propyl-hydrazide |

It should be further noted that a plurality of polymerizable linking agents may be used together to form an encapsulating net or linkage around an individual nanocrystal (or group of nanocrystals). This is of particular interest where the particular linking agent is incapable of forming a strong bond with the nanocrystal. Examples of linking agents capable of bonding together in such a manner to surround the nanocrystal with a network of linking agents include, but are not limited to: diacetylenes, styrene-butadienes, vinyl acetates, acrylates, acrylamides, vinyl, styryl, and the aforementioned silicon oxide, boron oxide, phosphorus oxide, silicates, borates and phosphates, as well as polymerized forms of at least some of the above.

e. Compounds and Probes having Three-Dimensional Structured Lining Agents

In one embodiment, the linking agent, including many of those described above, may be used in, or as, a three-dimensional structure which may be either organic or inorganic, and which may be either a solid (porous or non-porous) or hollow. In the prior art, the use of dye molecules embedded into latex spheres for diagnostic applications is well established. Perhaps the most common application involves selectively coloring the latex sphere using one or more dye molecules and then coating the sphere with a number of proteins of interest.

The utilization of such a three-dimensional linking agent structure (which may be most easily conceptualized as a sphere) in the compound and probe of the invention has the added benefit of permitting such a linking agent to have bonded thereto more than one semiconductor nanocrystals, as well as one or more affinity molecules (either directly or through a second linking agent). The three-dimensional linking agent structure will herein-after be described as a part of a probe (semiconductor nanocrystal, linking agent, and affinity molecule), it being understood that the structures described apply to the formation of a compound (semiconductor nanocrystal and linking agent) as well as a probe.

The advantage of a compound or probe in which one or more semiconductor nanocrystals are bonded to a three-dimensional linking agent structure lies in the ability to simultaneously use a large number of distinguishable probes. For example, when using emission of visible light as the detectable signal provided by the probe in response to exposure to radiation, multiple distinguishable probes, which each contain a single semiconductor nanocrystal of a respectively different emission color (e.g., blue probe, green probe, red probe) may be simultaneously used. Moreover, a much greater number of distinguishable probes may be simultaneously used when each probe contains a plurality of semiconductor nanocrystals, all bound to a single three-dimensional linking agent in the same probe (e.g., blue-green probe, green-red probe, blue-red probe, blue-green-red probe). Still further increases in combinations of semiconductor nanocrystals bonded to a three-dimensional linking agent structure can be achieved by varying the number of identically emitting semiconductor nanocrystals bonded to the three-dimensional linking agent in the same probe in order to provide different intensities of detectable signals (e.g. adding a second blue-emitting semiconductor nanocrystal to a blue-red probe to obtain a blue-blue-red probe, or adding another red-emitting semiconductor nanocrystal to a blue-red probe to achieve a blue-red-red probe). This further increases the total number of probes which can be simultaneously distinguished. Similar benefits can be obtained when the detectable signal or signals provided by the semiconductor nanocrystals in the probe result from scattering (including diffraction) or absorption resulting from exposure of the probe to radiation.

Similar to the incorporation of multiple semiconductor nanocrystals in a single three-dimensionally structured linking agent, multiple affinity molecules may be linked to the same three-dimensional liming agent structure to allow a plurality of detectable structures (including combinations of detectable structures) to be distinguishably and simultaneously detected by each semiconductor nanocrystal probe.

In an illustration of the use of multiple affinity molecules in each semiconductor nanocrystal probe in testing for Down's syndrome, a subset of the DNA sequences present on a particular chromosome in the human body, such as chromosome 21, may serve as the affinity molecules of a semiconductor nanocrystal probe when attached, in the form of a plurality of separate single stranded DNA fragments, to a three-dimensionally structured linking agent linked to one or more red emitting nanocrystals. A subset of the DNA sequences present on a different chromosome, such as chromosome 3, may serve as the single stranded DNA affinity molecules of another probe when similarly attached to a different three-dimensionally structured linking agent linked to one or more green emitting nanocrystals. A material comprising a total DNA sample from a human patient (or an amniocentesis sample), wherein are present one or more detectable substances in the form of single stranded DNA, may be treated with these semiconductor nanocrystal probes, resulting in the bonding of the single stranded DNA affinity molecules of the probes with the single stranded DNA detectable substances. This bonding results in the formation of double stranded DNA (in one or both probes), indicative of the presence of one or more DNA sequences (i.e., DNA sequences represented by the single stranded DNA detectable substances) in the DNA sample. This step may be followed with a step of detecting the bonding of the single stranded DNA affinity molecules with the single stranded DNA detectable substances by, for example, adding to the material, which contains the detectable substances and has been treated with the semiconductor nanocrystal probes, a double stranded DNA-binding dye molecule (which may fluoresce blue). The amount of double stranded DNA-binding dye molecules present (determined by amount of blue fluorescence) on a semiconductor nanocrystal probe, may be indicative of the amount of double stranded DNA associated with the semiconductor nanocrystal probe. Thus, the blue fluorescence from the probe containing DNA from chromosome 21 indicates the bonding of single stranded DNA affinity molecules from chromosome 21 with complementary single stranded DNA detectable substances from chromosome 21, to form double stranded DNA; and the blue fluorescence from the probe containing DNA from chromosome 3 indicates the bonding of single stranded DNA affinity molecules from chromosome 3 with complementary single stranded DNA detectable substances from chromosome 3, to form double stranded DNA.

In this test for Down's Syndrome, the semiconductor nanocrystal probe comprising single stranded DNA affinity molecules from chromosome 3, which emits green light, may serve as a reference probe, wherein the ratio of emitted green light to emitted blue light represents the reference amount of double stranded DNA present on a semiconductor nanocrystal probe. The semiconductor nanocrystal probe comprising single stranded DNA affinity molecules from chromosome 21, which emits red light, may serve as the test probe, wherein the ratio of emitted red light to emitted blue light (from the test probe) may be compared to the ratio of green light to blue light from the reference probe. A difference between the test and reference ratios may indicate extra or fewer copies of the test chromosome (chromosome 21), in this case indicating Down's Syndrome. The number of such tests which may be simultaneously performed may be significantly increased by the use of a plurality of colors in each of a plurality of semiconductor nanocrystal probes.

As stated above, the three-dimensional linking agent structure may comprise an organic or inorganic structure, and may be a porous or non-porous solid, or hollow. When the three-dimensional linking agent structure is a porous (or non-porous) solid the semiconductor nanocrystal may be embedded therein, while the semiconductor nanocrystal may be encapsulated in a hollow three-dimensional linking agent structure. Whatever the choice of material, it will be appreciated that whenever the semiconductor nanocrystal is incorporated into the interior of the three-dimensional structure of the linking agent, e.g., into a "polymer sphere", the material comprising the linking agent must both (1) allow a first energy to be transferred from an energy source to the one or more semiconductor nanocrystals (exposing the semiconductor nanocrystal to energy), and (2) allow a second energy, provided by the one or more semiconductor nanocrystals in response to exposure to the first energy, to be either detected or transferred to a proximal structure. These transfers of energy may be accomplished by the three-dimensional linking agent being transparent to the first and/or second energies, and/or by the three-dimensional linking agent being capable of converting the first and/or second energies to a form which still enables the semiconductor nanocrystal probe to either provide a detectable signal or transfer energy to a proximal structure in response to exposure to energy.

When the three-dimensional linking agent comprises an organic material, the organic material may comprise, for example, one or more resins or polymers. The semiconductor nanocrystals may be linked to the three-dimensional linking agent by physically mixing the semiconductor nanocrystals with the resin(s) or polymer(s), or may be mixed with the monomer(s) prior to polymerization of the monomer(s) to form the polymer(s). Alternatively, the semiconductor nanocrystals may be linked to the three-dimensional linking agent by covalent bonding to either the monomer or the resin or polymer, or the semiconductor nanocrystals may be linked to the three-dimensional linking agent by adsorption (adherence to the exterior) or absorption (embedded, at least partially, into the interior). Examples of polymers which could be used as organic three-dimensional linking agents include polyvinyl acetate, styrene-butadiene copolymers, polyacrylates, and styrene-divinylbenzene copolymers. More than one polymeric chain may be present in the three-dimensional linking agent, and more than one type of polymer may be used in the three-dimensional linking agent. The final product could be a solid structure, a hollow structure, or a semi-solid porous structure.

When the three-dimensional linking agent structure comprises an inorganic material, a glass structure such as a glass sphere could comprise the transparent structure used to encapsulate one or more semiconductor nanocrystals therein. The semiconductor nanocrystals could be mixed with particles of a low melting point glass, with the mixture then heated to form the desired three-dimensional structure, e.g., a sphere. Alternatively, a porous glass such as a porous silica glass could be formed into a desired shape (or applied over a solid substrate as a porous coating), followed by incorporation of the semiconductor nanocrystals into the pores of the linking agent structure. The previously described glass-coated semiconductor nanocrystals could also be modified to provide the three-dimensional linking agent structure of this embodiment, for example by providing the glass coating over a core of such semiconductor nanocrystals or by sintering into a three-dimensional mass a plurality of such glass coated semiconductor nanocrystals comprising the same or different semiconductor nanocrystals.

An additional increase in the number of three-dimensional structured probes which can be distinguishably used may arise from placing one or more identical semiconductor nanocrystals in one of a plurality of substructures of the three-dimensionally structured probe, and organizing the various substructures of the probe in such a manner to allow a large number of uniquely identifiable probes to be formed. For example, in a single probe, the three-dimensional structured linking agent may comprise a first semiconductor nanocrystal in a first polymer comprising a first substructure, and a second semiconductor nanocrystal in a second polymer immiscible with the first substructure comprising second substructure.

One example of the arrangement of these substructures is a manner analogous to the various layers of an onion. In such a construction, different arrangements of several differently emitting semiconductor nanocrystals positioned in the various substructure layers may be distinguished from one another. Therefore, a probe containing an inner core of blue semiconductor nanocrystals, encapsulated by a first substructure layer of red semiconductor nanocrystals, which is encapsulated by a second substructure layer of green semiconductor nanocrystals may be distinguished from a probe containing an inner core of green semiconductor nanocrystals, encapsulated by a first substructure layer of blue semiconductor nanocrystals, which is encapsulated by a second substructure layer of red semiconductor nanocrystals. Thus, arranging the different substructures of the semiconductor nanocrystal probe further increases the number of distinguishable probes which may be simultaneously used.

Additionally, various probes whose substructures are assembled in different arrangements may be distinguished. For example, a probe which comprises red, green and blue semiconductor nanocrystal substructures ordered in an onion-like arrangement may be distinguished from a probe which comprises red, green, and blue semiconductor nanocrystal substructures ordered in a soccer ball-like arrangement.

Therefore, there are a number of different manipulations of the semiconductor nanocrystals in the probe which results in a very large number of distinguishable probes. These manipulations include: varying the combinations of different semiconductor nanocrystals in the probe, varying the concentrations of similar and different semiconductor nanocrystals in the probe, incorporating semiconductor nanocrystals into a plurality of substructures in the probe, and varying the arrangement of such substructures containing semiconductor nanocrystals in the probe.

The incorporation of multiple nanocrystals and/or multiple affinity molecules into a single probe can be demonstrated in the use of the probes as the stationary phase in a screen for various nucleic acid sequences, where the nucleic acid sequences in the material being analyzed constitute the mobile phase.

A plurality of probes can be prepared which may each comprise a unique combination of semiconductor nanocrystals with similar or varied emission wavelengths. Associated with each probe having a unique semiconductor nanocrystal combination is a unique combination of one or more affinity molecules comprising one or more known nucleic acid sequences. In this context, the term "nucleic acid sequence" should be understood to include single or double stranded ribonucleic acid (RNA) or deoxyribonucleic acid (DNA) molecules or chemical or isotopic derivatives thereof, each molecule comprising two or more nucleic acid monomers. A plurality of unidentified nucleic acid sequences comprising the detectable substances in a mobile phase material being analyzed may now be exposed to the above described plurality of probes, e.g. flowed over the stationary phase probes.

The detection, i.e., the identification of the nucleic acid sequences in the mobile phase bound to the probes involves two aspects. First of all the occurrence of a bonding event must be ascertained. Secondly the identification of which probe, and therefore which nucleic acid sequence or sequences (affinity molecules) of the probe, are bound to the nucleic acid sequences being analyzed. The bonding event itself may be determined by detection of a tag (e.g., a dye molecule) which has been previously attached onto all of the nucleic acid sequences being analyzed. When bonding occurs, the presence of the tag will correspond spatially to a certain probe or probes. The identification of the type of nucleic acid sequence or sequences may be determined by the detection of the signal which corresponds to a unique combination of semiconductor nanocrystals within the probe or probes involved in the bonding. For example, the probes and material being analyzed may be exposed to radiation of a type which will result in provision of detectable signals from both the dye molecule and the particular probe or probes bonded to the mobile phase nucleic acid sequences. A spatially identifiable group of signals from both the dye molecules and semiconductor nanocrystals can then be detected. The first signal, emanating from the nucleic acid sequences being identified, signifies the presence of a bonded nucleic acid sequence or sequences of any sequence type. The second detectable signal, emanating from the probe (and the semiconductor nanocrystals therein), identifies the type of nucleic acid sequence or sequences which are bonded to the probe, by virtue of the known type of nucleic acid sequence or sequences forming the affinity molecule(s) of the probe.

For example, the material being analyzed and the probes could be exposed to electromagnetic radiation from a laser light source of a frequency at which the dye is excitable and which will also excite the semiconductor nanocrystals in the probe. The resulting detectable signals from the dye molecules and the probe or probes, could be visible light emissions of one or more frequencies signifying the presence of bonded nucleic acid sequences (the light from the dye molecules) and the identity of the particular probe bonded thereto (the light from the semiconductor nanocrystals in the probe). When the spatial locations of both the dye molecule emission and the probe emission correspond, this would signify the presence of particular nucleic acid sequences bonded to particular probes known to emit light of the detected frequencies.

Thus, once bonded to one or more nucleic acid sequences from the mobile phase being analyzed, a plurality of similar or different probes may then be identified according to the unique combination of semiconductor nanocrystals present in each probe. The probes may be identified either one after the other or simultaneously. The identification of each probe then allows the identification of the unique nucleic acid sequence or combination of nucleic acid sequences bound to the probe by way of the known nucleic acid sequence comprising the affinity molecule on the surface of each probe. In this way, a large number of different nucleic acid sequences may be rapidly screened and identified.

It should be noted that while it is contemplated that each affinity molecule comprising a unique, known nucleic acid sequence or sequences will be specifically bonded to a particular unidentified nucleic acid sequence or sequences being analyzed for, thus making identification precise, other uses may be contemplated. For example, a probe could be designed having, as its affinity molecule portion, a particular known nucleic acid sequence or sequences which would be bondable to an entire group of related unidentified nucleic acid sequences, thus permitting use of the probe as a broad identification or screening agent.

f. Exposure of the Probe to Energy and Detection of Emission/Absorption/Scattering Upon exposure of the semiconductor nanocrystal probe to energy, some or all of the energy may be transferred to the semiconductor nanocrystal probe. In response to exposure to this energy, the semiconductor nanocrystal probe may provide a plurality of detectable signals. These detectable signals include (1) emission of electromagnetic radiation, (2) absorption of radiation, and (3) scattering, including diffraction, of radiation.

The emission properties of the semiconductor nanocrystal probe may be very useful in a plurality of applications. As previously mentioned, the semiconductor nanocrystal probe of the invention is capable of being excited over a broad bandwidth, yet exhibits emission in a narrow wavelength band, in contrast to the dye molecules used in the prior art. Thus electromagnetic radiation of wavelength ranging from x-ray to ultraviolet to visible to infrared waves may be used to excite the semiconductor nanocrystals in the probe. In addition, the semiconductor nanocrystals are capable of excitation from bombardment with a particle beam such as an electron beam (e-beam). Furthermore, because of the broad bandwidth at which the semiconductor nanocrystals are excitable, one may use a common excitation source for the simultaneous excitation of several probes, e.g., several probes which give off radiation at different frequencies, thus permitting simultaneous excitation and detection of the presence of several probes indicating, for example, the presence of several detectable substances in the material being examined.

Thus, for example, a laser radiation source of a given frequency, e.g., blue light, may be used to excite a first semiconductor nanocrystal probe capable of emitting radiation of a second frequency, e.g., red light, indicating the presence, in the material being illuminated, of a first detectable substance to which the particular red light-emitting semiconductor nanocrystal probe has bonded. At the same time, the same blue light laser source may also be exciting a second semiconductor nanocrystal probe (in the same material) capable of emitting radiation of a third frequency, e.g., green light, indicating the presence, in the material being illuminated, of a second detectable substance to which the particular green light-emitting semiconductor nanocrystal probe has bonded. Thus, unlike the prior art, multiple excitation sources need not be used (because of the broad bandwidth in which the semiconductor nanocrystal probe of the invention is capable of being excited), and the narrow band of emission of the specific semiconductor nanocrystals in each probe makes possible the elimination of sequencing and/or elaborate filtering to detect the emitted radiation.

Another detectable signal provided by a semiconductor nanocrystal probe in response to radiation is absorption. The presence of the semiconductor nanocrystal probe, bound to a detectable substance in a biological material, may be indicated by detection of absorption of radiation by the semiconductor nanocrystal probe. Since the semiconductor nanocrystal probe has such a wide wavelength band of absorption, detection of the semiconductor nanocrystal probe may be carried out over a wide range of wavelengths, according to the requirements of the detection process. For example, many biological materials strongly absorb visible and ultraviolet radiation, but do not strongly absorb x-ray radiation. Such a biological material containing a detectable substance may be treated with a semiconductor nanocrystal probe. Presence of the semiconductor nanocrystal probe bonded with the detectable substance may then be indicated by detection of an absorption of x-rays.

The semiconductor nanocrystal probe of the invention may also provide a detectable scattering signal in response to exposure to energy. This detectable scattering signal may be a diffraction signal. Thus, for example, presence of a detectable substance within a material treated with a semiconductor nanocrystal probe (wherein the semiconductor nanocrystal probe is bonded to the detectable substance) may be indicated by the detection of a change in the scattering cross section or in diffraction of radiation upon exposure of the material to radiation.

The semiconductor nanocrystal probe of the invention may also be used in such a way that, instead of providing a detectable signal in response to radiation, it transfers energy to a proximal structure. This proximal structure, in response to the energy transfer, may then (1) provide a detectable signal, (2) undergo chemical or conformational changes, (3) transfer energy to a second proximal structure, or (4) any combination thereof. This may be achieved by introducing the semiconductor nanocrystals and the material together by any of the above methods, and then exposing the material to energy. It should be noted that a proximal source may be used to transfer energy from the proximal source to the probe (as will be described below) in contrast to the aforesaid transfer of energy from the probe to a proximal structure.

g. General use of the Probe

In general, the probe may be used in treating a material to determine the presence of a detectable substance by introducing the probe, for example, dispersed in a suitable carrier such as an aqueous solution (e.g., an saline solution), into the material to permit the affinity molecule of the probe to bond to the detectable substance (if such detectable substance is present in the material). After introduction of the probe into the material, unbonded probes may be optionally removed from the material, leaving only bonded probes. In either event, the material (and probes therein) may be exposed to an energy source capable of causing the probe(s) to provide a detectable signal. When the unbonded probes have not been removed, presence of the bonded probes can be determined (and distinguished from the unbonded probes) by a plurality of methods, including determining the spatial segregation of more intense detectable signals arising as a result of the localization of the bonded probes, as opposed to random dispersion (resulting in spatially random detectable signals) of the unbonded semiconductor nanocrystal probes.

As an alternative to adding the semiconductor nanocrystal probe to the material, the material may be in a carrier, such as an aqueous solution, and this material may be introduced into a compartment containing the semiconductor nanocrystal probe. The semiconductor nanocrystal probe may itself be in a carrier, or may be attached to a solid support. Presence of the detectable substance within the material may be determined by any method which is capable of indicating the bonding of the affinity molecule of the probe to the detectable substance. This may be accomplished, for example, by separating components of the material and exposing the components of the material to radiation, wherein a semiconductor nanocrystal probe, if present, may provide a detectable signal in response to exposure to radiation.

The carrier mentioned above is any type of matter that has little or no reactivity with the semiconductor nanocrystal probe, and enables storage and application of the semiconductor nanocrystal probe to the material to be treated. Such a material will often be a liquid, including many types of aqueous solutions, including biologically derived aqueous solutions (e.g. plasma from blood). Other liquids include alcohols, amines, and any other liquid which in neither reacts with nor causes the dissociation of the components of the semiconductor nanocrystal probe. The carrier also comprises a substance which will not interfere with the treatment or analysis being carried out by the probe in connection with the detectable substance in the material.

A further use of the semiconductor nanocrystal probe of the invention is to provide a detectable signal in response to energy transferred from one or more spatially proximal sources. In this context, "energy transfer" is meant the transfer of energy from one atom, molecule, or any other substance (e.g. a polymer, a gel, a lipid bilayer, etc.) to another atom, molecule, or any other substance by either (1) a radiative pathway (e.g., emission of radiation by a first atom or molecule followed by scattering—including diffraction—and/or absorption of the emitted radiation by a second atom or molecule); or (2) a non-radiative pathway (e.g., fluorescence resonance energy transfer, or FRET, from a first atom or molecule to a second atom or molecule). By use of the term "proximal source" is meant an atom, a molecule, or any other substance which is capable of transferring energy to and/or receiving energy transferred from another atom or molecule or any other substance. By use of the term "spatially proximal source" is meant a proximal source spaced sufficiently close to enable energy to be transferred from a proximal source to a semiconductor nanocrystal probe. For example, in the case of FRET, a spatially proximal source comprises a proximal source spaced 10 nm or less from the semiconductor nanocrystal probe. In the case of the transfer of radioactive energy, a spatially proximal source comprises a proximal source spaced 1 $\mu$m or less from the semiconductor nanocrystal probe.

The energy transferred from a proximal source to the semiconductor nanocrystal probe may originate from the proximal source (e.g., radioactive decay of an atom or atoms within the proximal source) or may arise as a result of excitation by an energy source separate from the proximal source (e.g., excitation of a proximal source dye molecule by a laser) as will be explained below. An illustration of a radiative pathway of energy transfer is the transfer of gamma radiation from a radioactive nucleus (of the proximal source) to a semiconductor nanocrystal probe. The transferred gamma radiation may then be absorbed by the semiconductor nanocrystal probe, which, in response to absorption of the gamma radiation, provides a detectable emission signal of electromagnetic radiation. An illustration of a non-radiative pathway is activation of the semiconductor nanocrystal by a FRET from a proximal source which has been externally excited, as will be described below.

Such a spatially proximal energy transfer may be useful in measuring the concentration of the proximal source, as well as the distance of the proximal source from the probe. Spatially proximal energy transfer can also be used in the detection of an event which causes the source from which energy is transferred to become spatially proximal to the probe.

One illustration of a spatially proximal energy transfer using a semiconductor nanocrystal probe is as a concentration indicator, wherein the semiconductor nanocrystal probe, in essence, acts as an energy transfer reporter. That is, the semiconductor nanocrystal probe, for example, may provide a detectable emission signal, the strength of which is a function of the local concentration of proximal sources from which the energy is transferred. This permits the probe to be used to determine the concentration of proximal sources from which energy is transferred. A possible application of this method would be to measure the amount of a zinc finger protein, such as the RAG1 protein, synthesized by a cell during a specific length of time using a pulse-chase experiment. The cell mixture may be pulsed with an addition of radioactive zinc ions to the growth medium and may, after a specific length of time, be chased by addition of non-radioactive zinc ions in large excess (e.g., greater than 100-fold) of the radioactive zinc ions. Such a pulse-chase experiment will result in one or more radioactive zinc ions incorporated only in zinc containing proteins synthesized during the specified length of time between the pulse and the chase. The cells may then be lysed to yield a soluble cell extract comprising one or more zinc containing proteins. A semiconductor nanocrystal probe comprising an affinity molecule, such as an antibody, which selectively bonds to a particular zinc finger protein may then be added to the soluble cell extract, allowing the semiconductor nanocrystal probe to bond to the particular zinc finger protein. The concentration of the particular zinc finger protein, comprising one or more radioactive zinc ions, and acting as the proximal source from which energy is transferred, bonded to semiconductor nanocrystal probe may be indicated by a detectable signal provided by the semiconductor nanocrystal probe in response to energy transferred from the radioactive zinc ion of the bonded particular zinc finger protein.

Another illustration of a spatially proximal energy transfer using the semiconductor nanocrystal probe is as a distance indicator. The strength of the detectable signal, for example, an emission, from a semiconductor nanocrystal probe is a function of the distance (provided that the distance is less than about 1 $\mu$m) between the semiconductor nanocrystal probe and the proximal source from which energy is transferred. Therefore, the detectable signal provided by the semiconductor nanocrystal probe may serve as an indicator of the distance between the semiconductor nanocrystal probe and the proximal source from which energy is transferred. A possible application for this is in the ability to determine spatial proximity of individual subunits of a multi-subunit complex within a cell, such as a transcriptional initiation complex, a ribosome, a lipid-lipoprotein complex, etc. For example, a semiconductor nanocrystal probe may bond with a protein subunit of a ribosome, while a RNA subunit of the ribosome may be labeled with a radioactive phosphorous atom, which serves as the proximal source from which energy is transferred (in this illustration, the energy transferred from the proximal source to the semiconductor nanocrystal probe originates from the proximal source). Since the strength of the emission of a detectable signal is a function of the distance between the semiconductor nanocrystal probe and the proximal source from which energy is transferred, the signal provided by the semiconductor nanocrystal probe bonded to the protein subunit indicates the approximate distance between the portion of the protein subunit bonded to the semiconductor nanocrystal probe and the portion of the RNA which contains the radioactive phosphorus atom from which the energy is transferred.

The spatially proximal energy transfer use of the semiconductor nanocrystal probe also may be utilized to detect the occurrence of an event. This event, for example, may cause the source from which energy is transferred to be located spatially proximal to the semiconductor nanocrystal probe. Since the detectable signal is a function of the distance between the proximal source from which energy is transferred and the semiconductor nanocrystal probe, the signal provided by the semiconductor nanocrystal probe may yield information reflective of an event which causes the source to be sufficiently proximal (less than about 10 nm) to enable energy to be transferred from the proximal source to the semiconductor nanocrystal probe. By way of illustration, a semiconductor nanocrystal probe may bond with a thyroid hormone receptor molecule. A thyroid hormone such as thyroxine may be labeled with a radioactive iodine atom, which serves as the source from which energy is transferred. An event which causes the thyroxine to bond to the thyroid hormone receptor will also cause the radioactive iodine atom in the thyroxine to be spatially proximal to the semiconductor nanocrystal probe. Therefore, this bonding event will cause energy to be transferred from the radioactive iodine atom to the semiconductor nanocrystal probe which may provide a detectable signal in response to the energy transfer. The detectable response will thus serve as an indicator of the event of thyroxine bonding to the thyroid hormone receptor.

The energy transferred from one or more proximal sources to one or more semiconductor nanocrystal probes may either originate from the proximal source (as in the example of radioactive decay of an atom or atoms within the proximal source), or may arise as a result of excitation of the one or more proximal sources by an energy source separate from the proximal sources. By use of the term "energy source separate from the proximal source" is meant any source of radiation or any other energy which transfers energy to the proximal source. The energy source separate from the one or more proximal sources may either be spatially distant or spatially proximal to the proximal source from which energy is transferred to the semiconductor nanocrystal probe. Thus, the energy may be transferred from a spatially distant energy source such as, for example, a laser or particle beam; or the energy may be transferred from a second spatially proximal source from which second proximal source the energy transferred may either originate, or arise as a result of excitation by an energy source separate from the second proximal source. For example, a laser beam may be used to excite a second proximal source, the second proximal source then excites the first proximal source, and the first proximal source excites the semiconductor nanocrystal probe; or a second proximal source may be a radioactive atom which excites the first proximal source which excites the semiconductor nanocrystal probe. It will be understood that more than two proximal energy sources can be utilized to transfer energy in a cascading effect. Included in pathways of excitation of the proximal source by a separate source is the case where the separate source is a particle beam which, when the proximal source is exposed to the particle beam, may cause a nuclear event in the proximal source. The proximal source may then transfer energy to the semiconductor nanocrystal probe as a result of the nuclear event caused by exposure of the proximal source to the particle beam.

When the excitation of the proximal source arises as a result of energy transferred from a separate energy source (e.g., a laser beam) the energy transfer from the proximal source to the semiconductor nanocrystal probe may be accomplished by FRET, as previously mentioned. Thus, an energy source separate from the proximal source, such as a laser, may excite a proximal source. The proximal source, as a result of relaxing from an excited state, may transfer energy via fluorescence resonance energy transfer to the semiconductor nanocrystal probe when the proximal source is less than about 10 nm from the semiconductor nanocrystal probe. The semiconductor nanocrystal probe may then provide a detectable signal such as electromagnetic radiation in response to the energy transfer from the proximal molecule. An illustration of both the excitation of the proximal molecule by an energy source separate from the proximal energy source and the use of FRET as the pathway of energy transfer from the proximal source to the probe may be derived from the previously described ribosomal example. In contrast to the previous example which used an RNA subunit of the ribosome labeled with a radioactive phosphorus atom as the proximal source, a dye molecule may be attached to the RNA subunit instead of the radioactive phosphorous atom. The proximal source RNA subunit with attached dye molecule may then be excited by a separate source, for example a laser beam. The excited proximal source RNA subunit may transfer energy to a semiconductor nanocrystal probe by way of a non-radiative energy transfer pathway such as FRET, which may provide a detectable signal in response to the energy transferred from the proximal source RNA subunit.

The use of a proximal source to transfer energy to a semiconductor nanocrystal probe may be modified in such a way as to enable a proximal source to transfer energy to a plurality of semiconductor nanocrystal probes. By way of illustration, in the previous example using an RNA molecule labeled with a dye molecule as the proximal molecule, a plurality of RNA proteins may be labeled, each with a differently emitting semiconductor nanocrystal probe. Fluorescence resonance energy may be transferred from the dye molecule to one or more of the differently emitting semiconductor nanocrystal probes. The detectable signals provided by the one or more differently emitting semiconductor nanocrystal probes may then signify proximity between the dye and the one or more semiconductor nanocrystal probes.

Since semiconductor nanocrystals of specific wavelength emission may be selected for use in a particular probe, a semiconductor nanocrystal probe may be exposed to, for example, a radioactive atom emitting gamma radiation from a proximal source, and the wavelength of the emission from the semiconductor nanocrystal probe, in response to exposure to gamma radiation from the proximal source, may be selected to be ultraviolet radiation, according to the nature of the semiconductor nanocrystal within the semiconductor nanocrystal probe. Alternatively, the wavelength of the emission of the semiconductor nanocrystal in response to exposure to, for example, gamma radiation from the proximal source may be selected to be red light. The ability to provide multiple and selectable different emissions in response to exposure to the identical radiation allows a plurality of differently emitting semiconductor nanocrystal probes to be used simultaneously. The simultaneous use of a plurality of probes which each emit different wavelengths of electromagnetic radiation can be used, for example, in a configuration where proximity between a specific semiconductor nanocrystal probe and a source from which energy is transferred to the semiconductor nanocrystal probe may be determined by the specific wavelength of the emission from the semiconductor nanocrystal probe. For example, three semiconductor nanocrystal probes which differ in the visible light they emit (e.g., blue, green, and red emitting semiconductor nanocrystal probes) could be attached to portions of an association of molecules (e.g., an organelle). Presence of a certain molecule with a radioactive atom attached (therefore acting as the proximal source) in proximity to one specific semiconductor nanocrystal probe results in emission of a specific color, indicating proximity between the certain molecule and the specific semiconductor nanocrystal probe and its associated affinity molecule.

Similar to the use of multiple semiconductor nanocrystals, it is possible to use multiple proximal sources capable of transferring energy to one or more semiconductor nanocrystal probes.

Similar to the process in which energy is transferred from one or more proximal sources to one or more semiconductor nanocrystal probes, energy may also be transferred from one or more semiconductor nanocrystal probes to one or more proximal structures in response to exposure of the semiconductor nanocrystal probe to energy. The term "proximal structure" as used herein may be an atom, a molecule, or any other substance (e.g. a polymer, a gel, a lipid bilayer, and any substance bonded directly to a semiconductor nanocrystal probe) which is capable of receiving energy transferred from another atom or molecule or other substance (including a semiconductor nanocrystal probe). The proximal structure, in response to the energy transferred from the semiconductor nanocrystal probe, may (1) provide a detectable signal, (2) undergo chemical and/or conformational changes, (3) transfer energy to one or more second proximal structures, or (4) any combination thereof. As used herein, a "second proximal structure" is a proximal structure to which energy is transferred from a first proximal structure which has received energy from a semiconductor nanocrystal probe. The second proximal structure, in response to the energy transferred from the first proximal structure may (1) provide a detectable signal, (2) undergo chemical and/or conformational changes, (3) transfer energy to one or more third proximal structures (where a "third proximal structure" is one to which energy has been transferred from a second proximal structure), or (4) any combination thereof. It will be understood that the transfer of energy between proximal structures may be further extended beyond a third proximal structure in a cascading effect.

An illustration of the use of a semiconductor nanocrystal probe to transfer energy to a proximal structure which provides a detectable signal is as follows. A semiconductor nanocrystal probe may be used to provide an emission of a narrow wavelength band in the blue region of visible light in response to excitation over a broad wavelength band of radiation.

When this semiconductor nanocrystal probe is spatially proximal to a dye molecule (the dye molecule herein is acting as the proximal structure), the dye molecule may then become excited upon transfer of energy from the semiconductor nanocrystal probe. The excited dye molecule may then be capable of providing a detectable red light emission in response to excitation by the energy transfer from the semiconductor nanocrystal.

An illustration of the use of a semiconductor nanocrystal probe to transfer energy to a proximal structure which, in response to the energy transferred from the semiconductor nanocrystal probe, undergoes chemical changes, is the use of semiconductor nanocrystals to break covalent bonds. A semiconductor nanocrystal probe may be exposed to energy, and may then transfer energy to a proximal structure in response to the exposure to energy. The energy transferred may be, for example, electromagnetic radiation which is capable of inducing a photolytic cleavage (or photolysis) of a covalent bond in a proximal structure. This action of photolysis may also result in the detachment of a portion of the proximal structure. This detached portion of the proximal structure may be, for example, a molecule used for therapeutic purposes such as a molecule with cytotoxic properties. This use of the semiconductor nanocrystal probe to break covalent bonds may be controlled in a dosage specific manner, according to the extent of exposure of the semiconductor nanocrystal probe to radiation. This control of the exposure of the semiconductor nanocrystal probe to radiation may result in control of the energy transferred to the proximal structure, which controls the photolytic cleavage of the covalent bond, and ultimately controls the detachment of the portion of the proximal structure. Additionally, the portion of the proximal structure may be detached in a spatially specific manner, according to the specificity of the one or more affinity molecules of the semiconductor nanocrystal probe.

This use of the semiconductor nanocrystal probe to break covalent bonds in the proximal structure may be particularly effective when the energy transferred to the semiconductor nanocrystal probe has a long wavelength which is transparent to the material surrounding the semiconductor nanocrystal probe. For example, a semiconductor nanocrystal probe may be exposed to electromagnetic radiation from a laser which emits at a wavelength of 700 nm (infrared radiation). Materials such as biological materials absorb very little radiation at 700 nm, but a semiconductor nanocrystal probe may absorb radiation at 700 nm. It is common for photolytic cleavages to require ultraviolet radiation for activation. An advantage of the semiconductor nanocrystal probe of the invention is that it may be made to transfer energy corresponding to ultraviolet radiation when exposed to infrared radiation as a result of a process termed two-photon absorption. Two-photon absorption may occur when a semiconductor nanocrystal probe is exposed to radiation in such a way that it simultaneously absorbs two quanta of radiation (i.e., two photons), and the resultant level of excitation of the semiconductor nanocrystal probe is twice as large as the level of excitation the semiconductor nanocrystal probe would have if it had absorbed a single quantum of radiation. By the physical relationship between energy and wavelength of radiation ($E=hc/\lambda$, where E is energy, h and c are constants, and $\lambda$ is wavelength), a level of excitation, corresponding to two quanta of a first type of radiation with a certain wavelength, would correspond to the level of excitation caused by absorption of a single quantum of a second type of radiation with a wavelength half that of the first type of radiation. Thus, if a semiconductor nanocrystal probe simultaneously absorbs two photons with wavelength of 700 nm, the excitation level of the semiconductor nanocrystal probe will be the same as the excitation level of a semiconductor nanocrystal probe which absorbs a single photon with a wavelength of about 350 nm (ultraviolet radiation). A semiconductor nanocrystal probe which has been excited by two-photon absorption may thus transfer energy, for example, by emitting electromagnetic radiation with a shorter wavelength than the wavelength of the radiation to which the semiconductor nanocrystal probe was exposed.

As an illustration of the use of this two-photon absorption, a semiconductor nanocrystal probe, comprising one or more affinity molecules which may specifically bond to one or more detectable substances representative of the presence of a cancerous cell or tissue, may be exposed to radiation from an infrared laser emitting at 700 nm. This semiconductor nanocrystal probe may then be excited by the infrared radiation (through the process of two-photon absorption), and may then emit ultraviolet radiation (which has a shorter wavelength—e.g. about 350 nm). This emitted radiation in the ultraviolet range (or energy transferred by some other process, such as by FRET) may then cause a photolytic cleavage in a proximal structure, which results in a cytotoxic molecule being detached from the proximal structure and acting as a toxin to the cancerous cell or tissue.

Another illustration of the response to the energy transferred from the semiconductor nanocrystal probe to the proximal structure resulting in the proximal structure undergoing chemical or conformational changes may result when the energy transferred from the semiconductor nanocrystal probe to the proximal structure is heat energy. This transfer of heat energy may result in a conformational change such as the heat-induced denaturation of a protein. A semiconductor nanocrystal probe may be able to absorb radiation which is not absorbed by the material surrounding the semiconductor nanocrystal probe. In response to exposure of the semiconductor nanocrystal probe to radiation, the semiconductor nanocrystal probe may transfer heat energy to a proximal structure, resulting in a local heating of structures proximal to the semiconductor nanocrystal probe. In response to this local heating, the proximal structure may (1) undergo a chemical or conformational change, and/or (2) transfer energy to a second proximal structure. Thus, exposure of a material to radiation (to which radiation the material is transparent) may result in local heating within the material. The heat energy transferred from the semiconductor nanocrystal to the proximal structure may then result in chemical or conformational changes in the proximal structure, and/or some or all of the heat energy may be transferred to a second proximal structure which itself could undergo chemical or conformational changes and/or transfer some or all of the heat energy to a third proximal structure, and so on. As in the example of the photolytically detached cytotoxic molecule, use of the semiconductor nanocrystal probe to cause transfer of heat energy may be controlled in a dosage specific manner, according to the extent of exposure of the semiconductor nanocrystal probe to radiation. Additionally, the heat energy may be transferred in a spatially specific manner, according to the specificity of the one or more affinity molecules of the semiconductor nanocrystal probe.

The amount of heat energy transferred to a proximal structure from a semiconductor nanocrystal probe in response to exposure to radiation may be enough to generate a large amount of local heating due to the high degree of stability and the large extinction coefficients characteristic of nanocrystals. In a specific example of the extent of local heating which may occur, when semiconductor nanocrystals (which emit infrared radiation) are present in a tissue at a concentration of about 0.0001 grams of semiconductor nanocrystals per gram of tissue, and these nanocrystals are exposed to an ultraviolet excitation source (or a two photon absorption source capable of exciting with an ultraviolet excitation energy), the heat energy transferred by these semiconductor nanocrystals over 1,000,000 photocycles (about one second of exposure to a saturating laser) in response to exposure to radiation may cause the tissue to increase in temperature by about 25° C. This large amount of local heating may be, for example, great enough to kill local cells and tissue; and therefore this use of the semiconductor nanocrystal probe to transfer heat energy may be applied to the treatment of cancerous cells or other nefarious cells and tissues.

Energy transfer from one or more semiconductor nanocrystal probes to one or more proximal structures may take place in a manner similar to any of the previously described transfers of energy from one or more proximal sources to one or more semiconductor nanocrystal probes. Therefore, a semiconductor nanocrystal probe may transfer energy to a proximal structure by way of radiative or non-radiative (e.g., FRET) pathways. The energy transferred from a semiconductor nanocrystal probe to a proximal structure by a radiative pathway may include particle and electromagnetic radiation. The energy transfer from a semiconductor nanocrystal probe to a proximal structure may occur as a result of energy transferred from an energy source separate from the semiconductor nanocrystal probe. This energy source separate from the semiconductor nanocrystal probe may either be a spatially distant energy source such as, for example, a laser or particle beam; or the energy may be transferred from a spatially proximal source, as previously discussed. This includes, for example, a spatially distant energy source which may transfer energy to a spatially proximal source, which may transfer energy to a semiconductor nanocrystal probe, which may transfer energy to a proximal structure.

Prior to using a semiconductor nanocrystal probe in a process comprising exposure of the semiconductor nanocrystal probe to energy, the semiconductor nanocrystal probe may be used as a precursor which may be subjected to further synthetic steps. These further synthetic steps may result in formation of a modified semiconductor nanocrystal probe which has a different affinity molecule than the affinity molecule of the precursor semiconductor nanocrystal probe. For example, a semiconductor nanocrystal probe, having one or more nucleic acid monomers as its affinity molecule portion, may serve as a precursor (primer) in a process for synthesizing DNA in large amounts, such as polymerase chain reaction (PCR); and the final PCR product may be a modified semiconductor nanocrystal probe having an affinity molecule with a greater number of nucleic acid monomers than the affinity molecule of the precursor semiconductor nanocrystal probe. The synthetic steps to which the semiconductor nanocrystal probe may be subjected include, for example, any method of nucleic acid synthesis (by use of the term, "nucleic acid synthesis" it is meant any enzymatic process of synthesizing nucleic acid strands using nucleic acid monomers). In any such nucleic acid synthesis (including the above PCR case), the precursor semiconductor nanocrystal probe is understood to comprise one or more nucleic acid strands, each comprising a number of nucleic acid monomers sufficient to allow the precursor semiconductor nanocrystal to be used as a primer in a nucleic acid synthesis reaction such as PCR (the nucleic acid strands often having from 1 to about 50 nucleic acid monomers) as the one or more affinity molecules portion of the semiconductor nanocrystal probe. The term "nucleic acid strand" should be understood to include a plurality of single or double stranded ribonucleic acid (RNA) or deoxyribonucleic acid (DNA) molecules or chemical or isotopic derivatives thereof, each molecule comprising two or more nucleic acid monomers. This nucleic acid strand affinity molecule portion may be modified by extending the nucleic acid strands by addition of nucleic acid monomers according to the desired sequence of the nucleic acid synthesis (chains may vary in length from 1 more nucleic acid monomer than the precursor, or primer, to as much as 500,000 nucleic acid monomers, or more if desired). This modified semiconductor nanocrystal probe is understood to have all of the properties and potential uses of any semiconductor nanocrystal probe. That is, the modified semiconductor nanocrystal probe is capable of bonding with one or more detectable substances, and is capable of providing a detectable signal in response to exposure to energy. This may include, for example, use of the modified semiconductor nanocrystal probe (comprising an affinity molecule with a modified DNA sequence) as a fluorescent marker in a plurality of nucleic acid based assays, including DNA sequencing assays and hybridization assays such as fluorescence in-situ hybridization and comparative genomic hybridization.

Another advantage of the semiconductor nanocrystal probe (or a semiconductor nanocrystal compound) of the invention is in any process which involves elevated temperatures. As used herein, "elevated temperatures" are understood to include temperatures from room temperature (about 25° C.) up to the temperature at which the particular semiconductor nanocrystal probe undergoes thermal degradation. Typically this may occur at temperatures of about 150° C. or even as low as 100° C. Because of the high degree of thermal stability of the semiconductor nanocrystals, semiconductor nanocrystal probes (or semiconductor nanocrystal compounds) may withstand use at elevated temperatures, including use in processes which comprise thermal cycling steps (i.e., processes which comprise one or more steps in which the temperature is cycled between a low temperature and a high temperature, such as the aforementioned PCR). For example, as discussed above, a precursor semiconductor nanocrystal probe may be used in PCR, which requires multiple steps in which the temperature is cycled between a low temperature (the DNA synthesis step) and a high temperature (the DNA strand separation step). The high temperature of the PCR reaction mixture may be about 95° C., a temperature at which many dye molecules degrade. The thermal stability properties of the semiconductor nanocrystal probe enable it to withstand the thermal cycling of PCR.

In addition to the use of semiconductor nanocrystal probes in PCR, the advantage of the high degree of thermal stability of the semiconductor nanocrystal probes may be applied to any other processes which may require elevated temperatures, such as use in heat shock methods, or methods using thermostable organisms or biomolecules derived from thermostable organisms.

An illustration of the simultaneous use of a plurality of different semiconductor nanocrystal probes is when a plurality of semiconductor nanocrystal probes are used in flow cytometry analysis. Flow cytometry, as used in the prior art, involves contacting a material, containing cells, with one or more dyes, or dye conjugated affinity molecules, which are capable of detecting certain molecules or substances on the surface or interior of those cells. The presence of the dye molecules on the surface or interior of a cell (and, hence, the presence of the certain molecule with which the dye interacts) is detected by flowing the material through a compartment which is transparent to both the energy to which the material is exposed, and to the detectable signal provided by the dye in response to exposure to energy. As the cells are within the transparent compartment, the cells are exposed to energy, such as electromagnetic radiation, which is capable of being absorbed by the dye. The dye, as a result of exposure to the electromagnetic radiation, emits a detectable signal, such as electromagnetic radiation of a different wavelength than that to which the material is exposed. When a plurality of dyes are used to indicate the presence of a plurality of substances on the surface or interior of the cells, the material containing the cells may be flowed through a plurality of transparent compartments, and the presence of a plurality of different dyes may be tested one at a time (i.e. consecutively) or a few at a time (maximum of three simultaneous detections).

In accordance with the invention, instead of using a dye molecule, a material containing cells may alternatively be contacted with a semiconductor nanocrystal probe (actually a plurality of probe, but all providing the same detectable signal in response to energy). The semiconductor nanocrystal probe may bond to one or more detectable substances, if any are present, on the surface or interior of the cells, to which the affinity molecules of the semiconductor nanocrystal probe are capable of bonding. Detection of the presence of the semiconductor nanocrystal probe (and hence, the presence of one or more specific detectable substances to which the semiconductor nanocrystal probe is bonded) may take place by first contacting the material containing the cells with the semiconductor nanocrystal probe. The material is then flowed through a transparent compartment wherein the material is exposed to energy such as, for example, ultraviolet laser radiation. The presence of the semiconductor nanocrystal probe may be indicated by a detectable signal such as, for example, emission of red light, provided by the semiconductor nanocrystal probe in response to exposure to energy. Detection of the detectable signal provided by the semiconductor nanocrystal probe, therefore, may indicate the presence of one or more detectable substances, on the surface or interior of cells, to which the semiconductor nanocrystal probe is bonded.

Use of a plurality of groups of semiconductor nanocrystal probes (each of which groups provide the same detectable signal in response to exposure to energy) may be conducted in a manner similar to the above use of a single semiconductor nanocrystal probe. The material containing the cells may be contacted with a plurality of semiconductor nanocrystal probes, and the material is then flowed through a plurality of transparent compartments. In each compartment, the presence of a specific semiconductor nanocrystal probe bonded to one or more detectable substances may be indicated by a particular detectable signal provided by the specific semiconductor nanocrystal probe. However, unlike the prior art, since each separate semiconductor nanocrystal probe is capable of producing a detectable signal (in response to energy) which is distinguishable from the detectable signals produced by other semiconductor nanocrystal probes which have been exposed to the same energy, the presence of more than one semiconductor nanocrystal probe, each bonded to one or more different detectable substances, may be simultaneously detected in a single compartment.

Furthermore, methods of using one or more semiconductor nanocrystal probes to detect one or more detectable substances on the surface or interior of cells may not require flowing the material through a transparent compartment, thereby extending the use of the semiconductor nanocrystal probes to any cytometric method (i.e. any method which is used to detect the presence of detectable substances on the surface or interior of cells). Instead of flowing the cell-containing material through a transparent compartment, the presence of one or more of a plurality of semiconductor nanocrystal probes bonded to the cells may be detected by any to technique capable of detecting the signals from the different semiconductor nanocrystal probes in a spatially sensitive manner. Such spatially sensitive detection methods include, for example, confocal microscopy and electron microscopy, as well as the aforementioned flow cytometry.

The following examples will serve to further illustrate the formation of the semiconductor nanocrystal probes of the invention, as well as their use in detecting the presence of a detectable substance in a material such as a biological material.

EXAMPLE 1

To illustrate the formation of the semiconductor nanocrystal compound (comprising the semiconductor nanocrystals linked to a linking agent) 20 ml. of a 5 mM solution of (4-mercapto)benzoic acid was prepared with a pH of 10 using $(CH_3)_4NOH \cdot 5H_2O$. 20 mg of tris-octylphosphine oxide coated CdSe/CdS core/shell nanocrystals were added to the solution and stirred until completely dissolved. The resultant nanocrystal/linking agent solution was heated for 5 hours at 50–60° C. and then concentrated to a few ml by evaporation. Then an equal volume of acetone was added and the nanocrystals precipitated out of solution homogeneously. The precipitate was then washed with acetone, dried, and then can be stored.

The semiconductor nanocrystal compound prepared above can be linked with an appropriate affinity molecule to form the semiconductor nanocrystal probe of the invention to treat a biological material to determine the presence or absence of a detectable substance. That is, the semiconductor nanocrystal compound prepared above can be linked, for example, with avidin or streptavidin (as the affinity molecule) to form an semiconductor nanocrystal probe to treat a biological material to ascertain the presence of biotin; or the semiconductor nanocrystal compound prepared above can be linked with anti-digoxiginen to form an semiconductor nanocrystal probe to treat a biological material to ascertain the presence of digoxiginen.

EXAMPLE 2

To illustrate the formation of a semiconductor nanocrystal compound (comprising silica coated semiconductor nanocrystals linked to a linking agent) 200 $\mu$l of 3-(mercaptopropyl)-trimethoxysilane and 40 $\mu$l of 3-(aminopropyl)-trimethoxysilane were added to 120 ml of anhydrous 25 % (v/v) dimethylsulfoxide in methanol. The pH of this solution was adjusted to 10 using 350 $\mu$l of a 25% (w/w) solution of $(CH_3)_4)NOH$ in methanol. 10 mg of CdS or ZnS or ZnS/CdS coated CdSe nanocrystals were dissolved into this solution (prepared, in the case of CdS, by a technique such as the technique described in the aforementioned Peng, Schlamp, Kadavanich, and Alivisatos article; or in the case of ZdS, by the technique described by Dabbousi et al. in "(CdSe)ZnS Core-Shell Quantum Dots: Synthesis and Characterization of a Size Series of Highly Luminescent Nanocrystals," Journal of Physical Chemistry B 101 pp 9463–9475, 1997), stirred to equilibrate for several hours, diluted with 200 ml of methanol with 150 $\mu$l of a 25% (w/w) solution of $(CH_3)_4NOH$ in methanol, then heated to boiling for 30 minutes. This solution was then cooled and mixed with a 200 ml solution of 90% (v/v) methanol, 10% (v/v) water, containing 1.0 ml of 3-(trihydroxysilyl)propyl methylphosphonate, monosodium salt (42% w/w solution in water) and 40 $\mu$l of 3-(aminopropyl)trimethoxysilane. This solution was stirred for two hours, then heated to boiling for fewer than five minutes, then cooled. Once cool, a solution of 4 ml of chlorotrimethylsilane in 36 ml methanol, the pH of which had been adjusted to 10 using solid $(CH_3)_4NOH.5H_2O$, was mixed with the solution and stirred for one hour. This solution was then heated to boiling for 30 minutes, cooled to room temperature and stirred for several hours more. The solvent was evacuated partially in vacuo at 60° C. This solution can be precipitated to an oily solid with acetone. The semiconductor nanocrystal compound may then be redissolved in water, and in a variety of buffer solutions to prepare it for linking it to an affinity molecule to form the semiconductor nanocrystal probe of the invention to treat a biological material to determine the presence or absence of a detectable substance.

Thus, the invention provides an semiconductor nanocrystal probe containing a semiconductor nanocrystal capable, upon excitation by either electromagnetic radiation (of either narrow or broad bandwidth) or particle beam, of emitting electromagnetic radiation in a narrow wavelength band and/or absorbing energy and/or scattering or diffracting said excitation, thus permitting the simultaneous usage of a number of such probes emitting different wavelengths of electromagnetic radiation to thereby permit simultaneous detection of the presence of a number of detectable substances in a given material. The probe material is stable in the presence of light or oxygen, capable of being excited by energy over a wide spectrum, and has a narrow band of emission, resulting in an improved material and process for the simultaneous and/or sequential detection of a number of detectable substances in a material such as a biological material.

Having thus described the invention what is claimed is:

1. A semiconductor nanocrystal compound capable of linking to one or more affinity molecules and capable of, in response to exposure to a first energy, providing a second energy, said semiconductor nanocrystal compound comprising:
    a) one or more semiconductor nanocrystals, each capable of, in response to exposure to said first energy, providing said second energy; and
    b) one or more linking agents, at least a portion of which said linking agents are linked to said one or more semiconductor nanocrystals.

2. The semiconductor nanocrystal compound of claim 1 wherein said one or more semiconductor nanocrystals in said compound are capable of receiving said first energy by fluorescence resonance energy transfer (FRET).

3. The semiconductor nanocrystal compound of claim 1 wherein said one or more semiconductor nanocrystals in said compound are capable of providing said second energy by fluorescence resonance energy transfer (FRET).

4. The semiconductor nanocrystal compound of claim 1 wherein said one or more semiconductor nanocrystals in said compound are capable of receiving said first energy by exposure to radiation.

5. The semiconductor nanocrystal compound of claim 4 wherein each of said one or more semiconductor nanocrystals is capable of absorbing said radiation over a wide bandwidth.

6. The semiconductor nanocrystal compound of claim 1 wherein said second energy results from diffraction and/or scattering of said first energy by at least one of said one or more semiconductor nanocrystals.

7. The semiconductor nanocrystal compound of claim 1 wherein said second energy results from absorption of said first energy by at least one of said one or more semiconductor nanocrystals.

8. The semiconductor nanocrystal compound of claim 1 wherein said one or more semiconductor nanocrystals in said compound are capable of providing said second energy as electromagnetic radiation emitted by said semiconductor nanocrystals.

9. The semiconductor nanocrystal compound of claim 1 wherein each of said one or more linking agents is capable of linking to said one or more affinity molecules.

10. The semiconductor nanocrystal compound of claim 1 wherein said one or more linking agents include a glass coating on said one or more semiconductor nanocrystals, and said glass coating is capable of being linked to said one or more affinity molecules.

11. The semiconductor nanocrystal compound of claim 10 wherein said glass coating on said one or more semiconductor nanocrystals comprises a coating of silica glass.

12. The semiconductor nanocrystal compound of claim 1 wherein at least one of said one or more linking agents comprises:
    a) a first linking agent linked to at least one of said one or more semiconductor nanocrystals; and
    b) a second linking agent:
        i) linked to said first linking agent on said one or more semiconductor nanocrystals; and
        ii) capable of linking to said one or more affinity molecules.

13. The semiconductor nanocrystal compound of claim 1 comprising two or more semiconductor nanocrystals wherein, in response to exposure to said first energy, said second energy provided by a first of said two or more semiconductor nanocrystals is different than said second energy provided by a second of said two or more semiconductor nanocrystals.

14. A semiconductor nanocrystal compound capable of linking to one or more affinity molecules and capable of, in response to exposure to a first energy, providing a second energy, said semiconductor nanocrystal compound comprising:
    a) one or more semiconductor nanocrystals, each capable of, in response to exposure to said first energy, providing said second energy; and b) one or more first linking agents to which said one or more semiconductor nanocrystals are linked, each of said one or more first linking agents capable of linking to:
   i) one or more second linking agents; or
   ii) one or more affinity molecules.

15. The semiconductor nanocrystal compound of claim 14 wherein at least one of said one or more first linking agents comprises a three-dimensional shaped structure capable of having linked thereto said one or more semiconductor nanocrystals.

16. The semiconductor nanocrystal compound of claim 15 wherein said three-dimensional shaped structure is capable of being linked, by embedding, to said one or more semiconductor nanocrystals.

17. The semiconductor nanocrystal compound of claim 15 wherein said three-dimensional shaped structure is capable of being linked, by adherence, to said one or more semiconductor nanocrystals.

18. The semiconductor nanocrystal compound of claim 15 wherein said three-dimensional shaped structure further comprises one or more organic materials.

19. The semiconductor nanocrystal compound of claim 15 wherein said three-dimensional shaped structure further comprises one or more inorganic materials.

20. The semiconductor nanocrystal compound of claim 15 wherein said three-dimensional shaped structure comprises a porous solid structure which encapsulates said one or more semiconductor nanocrystals.

21. The semiconductor nanocrystal compound of claim 15 wherein said three-dimensional shaped structure comprises a non-porous solid structure which encapsulates said one or more semiconductor nanocrystals.

22. The semiconductor nanocrystal compound of claim 15 wherein said three-dimensional shaped structure comprises a hollow structure which encapsulates said one or more semiconductor nanocrystals.

23. The semiconductor nanocrystal compound of claim 15 wherein said three-dimensional shaped structure comprises a layered structure having two or more layers.

24. The semiconductor nanocrystal compound of claim 15 wherein said three-dimensional shaped structure comprises a medium transparent to:
   i) said first energy to which said one or more semiconductor nanocrystals is exposed; and
   ii) said second energy provided by said semiconductor nanocrystals in response to said exposure to said first energy.

25. The semiconductor nanocrystal compound of claim 15 wherein said three-dimensional shaped structure comprises a medium:
   i) capable of transferring said first energy to said one or more semiconductor nanocrystals; and
   ii) transparent to said second energy provided by said semiconductor nanocrystals in response to said exposure to said first energy.

26. A semiconductor nanocrystal compound capable of linking to one or more affinity molecules and capable of emitting electromagnetic radiation in a narrow wavelength band when exposed to radiation comprising:
   a) one or more semiconductor nanocrystals, each capable of emitting electromagnetic radiation in a narrow wavelength band when exposed to radiation; and
   b) one or more linking agents, each of said one or more linking agents linked to one or more of said semiconductor nanocrystals.

27. A semiconductor nanocrystal probe capable of, in response to a first energy, providing a second energy, comprising:
   a) one or more semiconductor nanocrystal compounds; and
   b) one or more affinity molecules linked to said one or more semiconductor nanocrystal compounds.

28. The semiconductor nanocrystal probe of claim 27 wherein said probe is capable of bonding with one or more detectable substances.

29. A semiconductor nanocrystal probe capable of bonding with one or more detectable substances and capable of, in response to exposure to a first energy, providing a second energy, said semiconductor nanocrystal probe comprising:
   a) one or more semiconductor nanocrystals, each capable of, in response to exposure to said first energy, providing said second energy;
   b) one or more first linking agents, to which said one or more semiconductor nanocrystals are linked, each of said one or more first linking agents capable of linking to:
      i) one or more second linking agents; or
      ii) one or more affinity molecules; and
   c) one or more affinity molecules linked either to said one or more second linking agents or to said one or more first linking agents, each of said one or more affinity molecules capable of selectively bonding to said one or more detectable substances.

30. The semiconductor nanocrystal probe of claim 29 wherein said one or more semiconductor nanocrystals in said probe are capable of receiving said first energy by fluorescence resonance energy transfer (FRET).

31. The semiconductor nanocrystal probe of claim 29 wherein said one or more semiconductor nanocrystals in said probe are capable of providing said second energy by fluorescence resonance energy transfer (FRET).

32. The semiconductor nanocrystal probe of claim 29 wherein said one or more semiconductor nanocrystals in said probe are capable of receiving said first energy by exposure to radiation.

33. The semiconductor nanocrystal probe of claim 32 wherein each of said one or more semiconductor nanocrystals is capable of absorbing said radiation over a wide bandwidth.

34. The semiconductor nanocrystal probe of claim 29 wherein said second energy results from diffraction and/or scattering of said first energy by at least one of said one or more semiconductor nanocrystals.

35. The semiconductor nanocrystal probe of claim 29 wherein said second energy results from absorption of said first energy by at least one of said one or more semiconductor nanocrystals.

36. The semiconductor nanocrystal probe of claim 29 wherein said semiconductor nanocrystal probe is capable of transferring said second energy from said semiconductor nanocrystal probe to one or more first proximal structures.

37. The semiconductor nanocrystal probe of claim 29 wherein said one or more semiconductor nanocrystals in said probe are capable of providing said second energy as electromagnetic radiation emitted by said one or more semiconductor nanocrystals.

38. The semiconductor nanocrystal probe of claim 29 wherein said one or more first linking agents include a glass coating on said one or more semiconductor nanocrystals, and said glass coating is capable of being linked to:

i) said one or more second linking agents; or ii) said one or more affinity molecules.

39. The semiconductor nanocrystal probe of claim 38 wherein said glass coating on said one or more semiconductor nanocrystals comprises a coating of silica glass.

40. The semiconductor nanocrystal probe of claim 29 wherein said one or more semiconductor nanocrystals comprise two or more semiconductor nanocrystals wherein, in response to exposure to said first energy, said second energy provided by a first of said two or more semiconductor nanocrystals is different than said second energy provided by a second of said two or more semiconductor nanocrystals.

41. The semiconductor nanocrystal probe of claim 40 wherein said two or more semiconductor nanocrystals comprise three or more semiconductor nanocrystals wherein, in response to exposure to said first energy, said second energy provided by a third of said three or more semiconductor nanocrystals is different than said second energies respectively provided by said first and said second of said three or more semiconductor nanocrystals.

42. The semiconductor nanocrystal probe of claim 29 wherein said one or more semiconductor nanocrystals comprise two or more semiconductor nanocrystals wherein, in response to exposure to said first energy, said second energy provided by a first of said two or more semiconductor nanocrystals is the same as said second energy provided by a second of said two or more semiconductor nanocrystals.

43. The semiconductor nanocrystal probe of claim 42 wherein said two or more semiconductor nanocrystals comprise three or more semiconductor nanocrystals wherein, in response to exposure to said first energy, said second energy provided by a third of said three or more semiconductor nanocrystals is different than said second energies respectively provided by said first and said second of said three or more semiconductor nanocrystals.

44. The semiconductor nanocrystal probe of claim 37 wherein said one or more semiconductor nanocrystals comprise two or more semiconductor nanocrystals wherein, in response to exposure to said first energy, said electromagnetic radiation emitted by a first of said two or more semiconductor nanocrystals is different than said electromagnetic radiation emitted by a second of said two or more semiconductor nanocrystals.

45. The semiconductor nanocrystal probe of claim 44 wherein said two or more semiconductor nanocrystals comprise three or more semiconductor nanocrystals wherein, in response to exposure to said first energy, said electromagnetic radiation emitted by a third of said three or more semiconductor nanocrystals is different than said electromagnetic radiation respectively emitted by said first and said second of said three or more semiconductor nanocrystals.

46. The semiconductor nanocrystal probe of claim 37 wherein said one or more semiconductor nanocrystals comprise two or more semiconductor nanocrystals wherein, in response to exposure to said first energy, said electromagnetic radiation emitted by a first of said two or more semiconductor nanocrystals is the same as said electromagnetic radiation emitted by a second of said two or more semiconductor nanocrystals.

47. The semiconductor nanocrystal probe of claim 46 wherein said two or more semiconductor nanocrystals comprise three or more semiconductor nanocrystals wherein, in response to exposure to said first energy, said electromagnetic radiation emitted by a third of said three or more semiconductor nanocrystals is different than said electromagnetic radiation respectively emitted by said first and said second of said three or more semiconductor nanocrystals.

48. The semiconductor nanocrystal probe of claim 29 wherein said semiconductor nanocrystal probe is capable of treating a biological material to determine the presence of said one or more detectable substances.

49. The semiconductor nanocrystal probe of claim 29 wherein said semiconductor nanocrystal probe is capable of treating an organic material to determine the presence of said one or more detectable substances.

50. The semiconductor nanocrystal probe of claim 29 wherein said semiconductor nanocrystal probe is capable of treating an inorganic material to determine the presence of said one or more detectable substances.

51. The semiconductor nanocrystal probe of claim 29 wherein said semiconductor nanocrystal probe is capable of being exposed to elevated temperatures.

52. The semiconductor nanocrystal probe of claim 29 wherein said semiconductor nanocrystal probe is capable of being exposed to temperatures up to about 150° C.

53. The semiconductor nanocrystal probe of claim 29 wherein said semiconductor nanocrystal probe is capable of being exposed to temperatures up to about 100° C.

54. The semiconductor nanocrystal probe of claim 29 wherein said one or more affinity molecules are capable of being modified by one or more synthetic steps to form a modified semiconductor nanocrystal probe.

55. The modified semiconductor nanocrystal probe of claim 54 wherein said one or more affinity molecules comprise one or more strands of nucleic acid.

56. The modified semiconductor nanocrystal probe of claim 55 wherein said one or more strands of nucleic acid have been modified by nucleic acid synthesis to form said modified semiconductor nanocrystal probe.

57. The modified semiconductor nanocrystal probe of claim 56 wherein said modified semiconductor nanocrystal probe is, prior to said nucleic acid synthesis step, exposed to an elevated temperature sufficient to cause said one or more strands of nucleic acid to separate.

58. The modified semiconductor nanocrystal probe of claim 57 wherein said one or more strands of nucleic acid have been modified by a polymerase chain reaction.

59. The semiconductor nanocrystal probe of claim 29 wherein at least one of said one or more semiconductor nanocrystals comprise an alloy comprising two or more semiconductors selected from the group consisting of Group III-V compounds, Group II-VI compounds, Group IV elements, and combinations of same.

60. The semiconductor nanocrystal probe of claim 29 wherein at least one of said one or more semiconductor nanocrystals comprise:

a) a core; and b) one or more shells, concentrically disposed around the core.

61. The semiconductor nanocrystal probe of claim 29 wherein said one or more affinity molecules comprise one or more first protein molecules, and said one or more detectable substances comprise one or more second protein molecules to which said one or more first protein molecules bond.

62. The semiconductor nanocrystal probe of claim 29 wherein said one or more affinity molecules comprise one or more first small molecules, and said one or more detectable substances comprise one or more second small molecules to which said one or more first small molecules bond.

63. The semiconductor nanocrystal probe of claim 29 wherein said one or more affinity molecules comprise one or more protein molecules, and said one or more detectable substances comprise one or more small molecules to which said one or more protein molecules bond.

64. The semiconductor nanocrystal probe of claim 29 wherein said one or more affinity molecules comprise one or more small molecules, and said one or more detectable substances comprise one or more protein molecules to which said one or more small molecules bond.

65. A semiconductor nanocrystal probe capable of bonding with one or more detectable substances and capable of providing one or more detectable signals in response to exposure to radiation comprising:
 a) one or more semiconductor nanocrystals, each capable of providing a detectable signal in response to exposure to radiation;
 b) one or more first linking agents, each of said one or more first linking agents having a first portion linked to at least one of said one or more semiconductor nanocrystals, and each of said one or more first linking agents having a second portion capable of linking to either one or more second linking agents or to one or more affinity molecules; and
 c) one or more affinity molecules linked either to said second linking agent or to said second portion of said one or more first linking agents, each of said one or more affinity molecules capable of selectively bonding to said one or more detectable substances.

66. The semiconductor nanocrystal probe of claim 65 wherein said one or more detectable signals provided by said one or more semiconductor nanocrystals in response to said exposure to radiation comprises electromagnetic radiation emitted in a narrow wavelength band.

67. A semiconductor nanocrystal probe capable of bonding with one or more detectable substances and capable of, in response to exposure to a first energy, providing a second energy, comprising:
 a) one or more semiconductor nanocrystals, each capable of, in response to exposure to said first energy, providing said second energy;
 b) one or more first linking agents, at least one of said one or more first linking agents comprising a three-dimensional shaped structure capable of having linked thereto said one or more semiconductor nanocrystals, each of said one or more first linking agents capable of linking to:
  i) one or more second linking agents; or
  ii) one or more affinity molecules; and
 c) one or more affinity molecules linked either to said one or more second linking agents or to said one or more first linking agents, each of said one or more affinity molecules capable of selectively bonding to said one or more detectable substances.

68. The semiconductor nanocrystal probe of claim 67 wherein said three-dimensional shaped structure is capable of being linked, by covalently bonding, to said one or more semiconductor nanocrystals.

69. The semiconductor nanocrystal probe of claim 67 wherein said three-dimensional shaped structure is capable of being linked, by adherence, to said one or more semiconductor nanocrystals.

70. The semiconductor nanocrystal probe of claim 67 wherein said three-dimensional shaped structure is capable of being linked, by embedding, to said one or more semiconductor nanocrystals.

71. The semiconductor nanocrystal probe of claim 67 wherein said three-dimensional shaped structure further comprises one or more organic materials.

72. The semiconductor nanocrystal probe of claim 67 wherein said three-dimensional shaped structure further comprises one or more inorganic materials.

73. The semiconductor nanocrystal probe of claim 67 wherein said three-dimensional shaped structure comprises a porous solid structure which encapsulates said one or more semiconductor nanocrystals.

74. The semiconductor nanocrystal probe of claim 67 wherein said three-dimensional shaped structure comprises a non-porous solid structure which encapsulates said one or more semiconductor nanocrystals.

75. The semiconductor nanocrystal probe of claim 67 wherein said three-dimensional shaped structure comprises a hollow structure which encapsulates said one or more semiconductor nanocrystals.

76. The semiconductor nanocrystal probe of claim 67 wherein said three-dimensional shaped structure comprises a spherically shaped structure.

77. The semiconductor nanocrystal probe of claim 67 wherein said three-dimensional shaped structure comprises two or more substructures wherein each substructure comprises one or more identical semiconductor nanocrystals.

78. The semiconductor nanocrystal probe of claim 77 wherein said two or more substructures each comprise a single layer in a layered structure.

79. The semiconductor nanocrystal probe of claim 67 wherein said three-dimensional shaped structure comprises a medium transparent to:
 i) said first energy to which said one or more semiconductor nanocrystals is exposed; and
 ii) said second energy provided by said semiconductor nanocrystals in response to said exposure to said first energy.

80. The semiconductor nanocrystal probe of claim 67 wherein said three-dimensional shaped structure comprises a medium:
 i) capable of transferring said first energy to said one or more semiconductor nanocrystals; and
 ii) transparent to said second energy provided by said semiconductor nanocrystals in response to said exposure to said first energy.

81. The semiconductor nanocrystal probe of claim 67 wherein each of said one or more affinity molecules comprises a molecule of one or more strands of nucleic acid, and each of said one or more detectable substances comprises a molecule of one or more strands of nucleic acid with which said probe bonds.

82. A process for forming a semiconductor nanocrystal compound capable of linking to one or more affinity molecules and capable of, in response to exposure to a first energy, providing a second energy, said semiconductor nanocrystal compound, said process comprising linking together:
 a) one or more semiconductor nanocrystals, each capable of, in response to exposure to said first energy, providing said second energy; and
 b) one or more linking agents.

83. The process for forming a semiconductor nanocrystal compound of claim 82 including the steps of:
 a) linking said one or more semiconductor nanocrystals to one or more first linking agents; and
 b) linking said one or more first linking agents to one or more second linking agents capable of linking to said one or more affinity molecules.

84. The process for forming a semiconductor nanocrystal compound of claim 82 which further comprises the steps of:
 a) forming a glass coating on said one or more semiconductor nanocrystals; and
 b) treating said glass coating with one or more linking agents capable of linking to said glass coating and also capable of linking to said one or more affinity molecules.

85. The process for forming a semiconductor nanocrystal compound of claim 82 which further comprises the steps of:
   a) forming a glass coating, as a first linking agent, on said one or more semiconductor nanocrystals; and
   b) treating said glass coating with one or more second linking agents capable of linking to said glass coating and also capable of linking to said one or more affinity molecules.

86. The process for forming a semiconductor nanocrystal compound of claim 82 wherein said step of linking said one or more semiconductor nanocrystals to said one or more first linking agents further comprises linking said one or more semiconductor nanocrystals to one or more three-dimensional shaped structures comprising said one or more first linking agents.

87. A process for forming a semiconductor nanocrystal probe capable of, in response to a first energy, providing a second energy, said process comprising linking together:
   a) one or more semiconductor nanocrystal compounds; and
   b) one or more affinity molecules.

88. A process for forming a semiconductor nanocrystal probe capable of bonding with one or more detectable substances and capable of, in response to exposure to a first energy, providing a second energy, said process comprising the steps of:
   a) linking one or more first linking agents with one or more semiconductor nanocrystals, said semiconductor nanocrystals each capable of, in response to exposure to said first energy, providing said second energy; and
   b) linking said one or more first linking agents to either:
      i) one or more second linking agents; or
      ii) one or more affinity molecules capable of selectively bonding to said one or more detectable substances; and
   c) linking said one or more affinity molecules to said one or more second linking agents when said one or more first linking agents are linked to said one or more second linking agents.

89. The process for forming a semiconductor nanocrystal probe of claim 88 wherein said step of linking together said one or more semiconductor nanocrystals and said one or more first linking agents is carried out prior to said steps of:
   a) linking said one or more first linking agents to either:
      i) said one or more second linking agents; or
      ii) one or more affinity molecules capable of selectively bonding to said one or more detectable substances; and
   b) linking said one or more affinity molecules to said one or more second linking agents when said one or more first linking agents are linked to said one or more second linking agents.

90. The process for forming a semiconductor nanocrystal probe of claim 88 wherein said steps of:
   a) linking said one or more first linking agents to either:
      i) said one or more second linking agents; or
      ii) said one or more affinity molecules capable of selectively bonding to said one or more detectable substances; and
   b) linking said one or more affinity molecules to said one or more second linking agents when said one or more first linking agents are linked to said one or more second linking agents;
are carried out prior to said step of linking together said one or more semiconductor nanocrystals and said one or more first linking agents.

91. The process for forming a semiconductor nanocrystal probe of claim 88 which further comprises the steps of:
   a) forming a glass coating, as a first linking agent, on said one or more semiconductor nanocrystals; and
   b) treating said glass coating with either:
      i) one or more of said second linking agents which are capable of linking to said glass coating; or
      ii) said one or more affinity molecules.

92. The process for forming a semiconductor nanocrystal probe of claim 88 wherein said step of linking said one or more semiconductor nanocrystals to said one or more first linking agents further comprises linking said one or more semiconductor nanocrystals to one or more three-dimensional shaped structures comprising said one or more first linking agents.

93. The process for forming a semiconductor nanocrystal probe of claim 92 wherein said three-dimensional shaped structure is formed by forming a layered structure having two or more layers.

94. The process for forming a semiconductor nanocrystal probe of claim 88 wherein at least one of said one or more affinity molecules comprises an affinity molecule capable of being treated in a further step to form a modified semiconductor nanocrystal probe.

95. The process for forming a modified semiconductor nanocrystal probe of claim 94 wherein said step of linking said one or more affinity molecules to either one or more first linking agents or one or more second linking agents further comprises linking said first or second linking agents to one or more strands of nucleic acid which comprise said one or more affinity molecules.

96. The process for forming a modified semiconductor nanocrystal probe of claim 95 comprising the further step of modifying said one or more strands of nucleic acid by nucleic acid synthesis to form said modified semiconductor nanocrystal probe.

97. The process for forming a modified semiconductor nanocrystal probe of claim 96 wherein:
   (a) each of said one or more strands of nucleic acid comprises from 1 to about 50 nucleic acid monomers; and
   (b) said nucleic acid synthesis comprises the addition of from 1 to about 500,000 nucleic acid monomers to said one or more strands of nucleic acid.

98. The process for forming a modified semiconductor nanocrystal probe of claim 96 wherein said step of modifying said one or more strands of nucleic acid by said nucleic acid synthesis further includes the step of exposing said semiconductor nanocrystal probe to an elevated temperature sufficient to cause said one or more strands of said nucleic acid to separate.

99. The process for forming a modified semiconductor nanocrystal probe of claim 98 wherein said step of modifying said one or more strands of nucleic acid by nucleic acid synthesis further comprises modifying said one or more strands of nucleic acid by a polymerase chain reaction.

100. In a process wherein a precursor semiconductor nanocrystal probe has already been formed by linking one or more semiconductor nanocrystals with one or more linking agents, and linking said one or more linking agents with one or more affinity molecules comprising one or more nucleic acid monomers, the further step which comprises subjecting said precursor probe to nucleic acid synthesis to form a modified semiconductor nanocrystal probe.

101. A process for treating a material by introducing one or more semiconductor nanocrystal probes into said material which comprises:

a) contacting said material with one or more semiconductor nanocrystal probes, said one or more semiconductor nanocrystal probes each comprising:
  i) one or more semiconductor nanocrystals, each capable of, in response to exposure to a first energy, providing a second energy;
  ii) one or more first linking agents, to which said one or more semiconductor nanocrystals are linked, each of said one or more first linking agents capable of linking to:
    1) one or more second linking agents; or
    2) one or more affinity molecules; and
  iii) one or more affinity molecules linked either to said one or more second linking agents or to said one or more first linking agents;
b) exposing said one or more semiconductor nanocrystal probes in said material to said first energy whereby said second energy is provided by said one or more semiconductor nanocrystals in said one or more semiconductor nanocrystal probes.

102. The process for treating a material of claim 101 wherein said one or more semiconductor nanocrystal probes are capable of bonding to one or more detectable substances in said material, and said second energy provided by said one or more semiconductor nanocrystal probes is indicative of the presence of said one or more detectable substances, in said material, bonded to said one or more semiconductor nanocrystal probes.

103. The process for treating a material of claim 101 wherein said one or more semiconductor nanocrystal probes are capable of transferring said second energy to one or more first proximal structures; and said process includes the further step of transferring said second energy from said one or more semiconductor nanocrystal probes to said one or more first proximal structures.

104. The process for treating a material of claim 103 comprising the further step of detecting a detectable signal provided by said one or more first proximal structures in response to said second energy transferred from said one or more semiconductor nanocrystal probes.

105. The process for treating a material of claim 104 wherein said one or more semiconductor nanocrystal probes transfer said second energy to said one or more first proximal structures by way of a non-radiative pathway.

106. The process for treating a material of claim 103 wherein at least one of said one or more first proximal structures undergoes a chemical change in response to said second energy transferred from said one or more semiconductor nanocrystal probes to said one or more first proximal structures.

107. The process for treating a material of claim 106 wherein said chemical change comprises a photolytic cleavage of one or more covalent bonds.

108. The process for treating a material of claim 106 wherein said first energy to which said semiconductor nanocrystal probe is exposed comprises radiation having a first wavelength, and said second energy transferred from said one or more semiconductor nanocrystal probes to said one or more first proximal structures comprises radiation having a second wavelength, wherein said second wavelength is shorter than said first wavelength.

109. The process for treating a material of claim 108 whereby said first energy having said first wavelength is converted to said second energy having said second shorter wavelength through a process of two-photon absorption.

110. The process for treating a material of claim 108 wherein said first energy to which said semiconductor nanocrystal probe is exposed comprises infrared radiation, and wherein said second energy transferred from said one or more semiconductor nanocrystal probes to said one or more first proximal structures comprises ultraviolet radiation.

111. The process for treating a material of claim 103 wherein at least one of said one or more first proximal structures undergoes conformational changes in response to said second energy transferred from said one or more semiconductor nanocrystal probes to said one or more first proximal structures.

112. The process for treating a material of claim 103 wherein said second energy transferred from said one or more semiconductor nanocrystal probes to said one or more first proximal structures is heat energy.

113. The process for treating a material of claim 103 wherein said second energy transferred from said one or more semiconductor nanocrystal probes to said one or more first proximal structures, is transferred from said one or more first proximal structures to one or more second proximal structures.

114. A process for treating a material using one or more semiconductor nanocrystal probes to determine the presence of one or more detectable substances in said material which comprises:
  a) contacting said material with one or more semiconductor nanocrystal probes, said one or more semiconductor nanocrystal probes each comprising:
    i) one or more semiconductor nanocrystals, each capable of, in response to exposure to a first energy, providing a second energy;
    ii) one or more first linking agents, to which said one or more semiconductor nanocrystals are linked, each of said one or more first linking agents capable of linking to:
      1) one or more second linking agents; or
      2) one or more affinity molecules; and
    iii) one or more affinity molecules linked either to said one or more second linking agents or to said one or more first linking agents, each of said one or more affinity molecules capable of selectively bonding to said one or more detectable substances;
  b) exposing said one or more semiconductor nanocrystal probes to said first energy; and
  c) detecting said second energy provided by said one or more semiconductor nanocrystals in said one or more semiconductor nanocrystal probes bonded to said one or more detectable substances in said material.

115. The process for treating a material of claim 114 further including the optional step of removing from said material any of said one or more semiconductor nanocrystal probes not bonded to said one or more detectable substances in said material prior to said step of detecting said second energy provided by any of said one or more probes bonded to said one or more detectable substances.

116. The process for treating a material of claim 115 wherein said one or more detectable substances, the presence of which is being determined, comprise a biological material.

117. The process for treating a material of claim 115 wherein said one or more detectable substances are present on the surface or interior of biological cells.

118. The process for treating a material of claim 117 wherein two or more of said semiconductor nanocrystal probes are bonded to said one or more detectable substances in said material, each of said two or more probes capable of providing a second energy comprising a detectable signal in response to exposure to said first energy, and at least two of said detectable signals from said two or more probes are simultaneously detected.

119. The process for treating a material of claim 117 wherein said material is flowed through one or more compartments transparent to:
   a) said first energy to which said material is exposed; and
   b) said second energy provided by said one or more semiconductor nanocrystal probes in response to exposure to said first energy.

120. The process for treating a material of claim 119 wherein two or more of said semiconductor nanocrystal probes are bonded to said one or more detectable substances in said material, each of said two or more probes capable of providing a second energy comprising a detectable signal in response to exposure to said first energy, and at least two of said detectable signals from said two or more probes are consecutively detected.

121. The process for treating a material of claim 119 wherein two or more of said semiconductor nanocrystal probes are bonded to said one or more detectable substances in said material, each of said two or more probes capable of providing a second energy comprising a detectable signal in response to exposure to said first energy, and at least two of said detectable signals from said two or more probes are simultaneously detected.

122. The process for treating a material of claim 115 wherein said one or more affinity molecules has been modified with an organic substance prior to said treating of said material.

123. The process for treating a material of claim 115 wherein said one or more affinity molecules comprise one or more strands of nucleic acid, and said one or more detectable substances in said material also comprise one or more strands of nucleic acid; and said step of contacting said material with said one or more probes causes said one or more strands of nucleic acid of said one or more probes to bond to said one or more strands of nucleic acid in said material by nucleic acid hybridization.

124. The process for treating a material of claim 115 wherein said first energy is transferred from one or more proximal sources to said one or more semiconductor nanocrystal probes.

125. The process for treating a material of claim 124 wherein said one or more proximal sources transfer said first energy to said one or more semiconductor nanocrystal probes by way of a radiative pathway.

126. The process for treating a material of claim 124 wherein said one or more proximal sources transfer said first energy to said one or more semiconductor nanocrystal probes by way of a non-radiative pathway.

127. The process for treating a material of claim 124 wherein said second energy indicates the concentration of at least one of said one or more proximal sources.

128. The process for treating a material of claim 124 wherein said second energy indicates the distance between at least one of said one or more proximal sources and at least one of said one or more semiconductor nanocrystal probes.

129. The process for treating a material of claim 124 wherein said second energy indicates an event which causes said one or more proximal sources to be spatially proximal to said one or more semiconductor nanocrystal probes.

130. The process for treating a material of claim 124 wherein said one or more proximal sources undergo nuclear decay; and said first energy to which said one or more semiconductor nanocrystals are exposed, comprises radiation originating from said one or more proximal sources.

131. The process for treating a material of claim 124 wherein said first energy to which said one or more semiconductor nanocrystals are exposed, is transmitted through said one or more proximal sources from an energy source separate from said one or more proximal sources.

132. The process for treating a material of claim 115 wherein at least one of said one or more first linking agents comprises a three dimensional structure.

133. The process for treating a material of claim 132 wherein said three dimensional structure is linked to two or more of said semiconductor nanocrystals.

134. The process for treating a material of claim 133 wherein said second energy provided by said two or more semiconductor nanocrystals linked to said three dimensional structure comprises one or more detectable signals.

135. The process for treating a material of claim 115 wherein said one or more semiconductor nanocrystal probes comprise two or more semiconductor nanocrystal probes; and wherein, in response to exposure to said first energy, said second energy provided by a first of said two or more semiconductor nanocrystal probes is different than said second energy provided by a second of said two or more semiconductor nanocrystal probes.

136. The process for treating a material of claim 135 wherein said two or more semiconductor nanocrystal probes comprise three or more semiconductor nanocrystal probes wherein, in response to exposure to said first energy, said second energy provided by a third of said three or more semiconductor nanocrystal probes is different than said second energies respectively provided by said first and said second of said three or more semiconductor nanocrystal probes.

137. The process for treating a material of claim 115 wherein said one or more semiconductor nanocrystal probes comprise two or more semiconductor nanocrystal probes wherein, in response to exposure to said first energy, said second energy provided by a first of said two or more semiconductor nanocrystal probes is the same as said second energy provided by a second of said two or more semiconductor nanocrystal probes.

138. The process for treating a material of claim 137 wherein said two or more semiconductor nanocrystal probes comprise three or more semiconductor nanocrystal probes wherein, in response to exposure to said first energy, said second energy provided by a third of said three or more semiconductor nanocrystal probes is different than said second energies respectively provided by said first and said second of said three or more semiconductor nanocrystal probes.

139. A process for treating a material to determine the presence of one or more detectable substances in said material which comprises:
   a) contacting said material with one or more semiconductor nanocrystal probes capable of bonding with said one or more detectable substances, if present, in said material, and capable of providing one or more detectable signals in response to exposure to energy, said one or more semiconductor nanocrystal probes comprising:
      i) one or more semiconductor nanocrystals each capable of providing a detectable signal in response to exposure to energy;
      ii) one or more first linking agents, to which said one or more semiconductor nanocrystals are linked, each of said one or more first linking agents capable of linking to:
         1) one or more second linking agents; or
         2) one or more affinity molecules; and
      iii) one or more affinity molecules linked either to said one or more second linking agents or to said one or more first linking agents, each of said one or more affinity molecules capable of selectively bonding to said one or more detectable substances;

b) optionally removing, from said material, any of said semiconductor nanocrystal probes not bonded to said one or more detectable substances; and c) exposing said material to energy capable of causing said one or more semiconductor nanocrystals to provide one or more detectable signals in response to said energy, indicative of the presence of said one or more detectable substances in said material; and d) detecting said one or more detectable signals provided by said one or more semiconductor nanocrystals in said one or more semiconductor nanocrystal probes.

140. The process for treating a material of claim 139 wherein said step of exposing said material to energy capable of causing said one or more semiconductor nanocrystals to provide one or more detectable signals further comprises exposing said material to a source of radiation.

141. The process for treating a material of claim 140 wherein said source of radiation comprises a source of electromagnetic radiation.

142. The process for treating a material of claim 141 wherein said source of electromagnetic radiation is capable of emitting electromagnetic radiation of a broad or narrow wavelength band.

143. The process for treating a material of claim 142 wherein said broad or narrow wavelength band of electromagnetic radiation comprises electromagnetic radiation selected from the group consisting of visible light, ultraviolet light, x-rays, and infrared light.

144. The process for treating a material of claim 140 wherein said source of radiation comprises a particle beam.

145. The process for treating a material of claim 139 wherein said one or more detectable signals result from diffraction and/or scattering of said energy by at least one of said one or more semiconductor nanocrystals.

146. The process for treating a material of claim 145 wherein said step of exposing said material to energy capable of providing said one or more detectable signals from diffraction and/or scattering of said energy further comprises exposing said material to a particle beam.

147. The process for treating a material of claim 145 wherein:

a) said step of exposing said materials to energy capable of causing said one or more semiconductor nanocrystals to scatter or diffract energy; and b) said step of detecting said one or more detectable signals resulting from said scattering or diffraction of energy;

are both carried out using a transmission electron microscope.

148. The process for treating a material of claim 145 wherein:

a) said step of exposing said materials to energy capable of causing said one or more semiconductor nanocrystals to scatter or diffract energy; and b) said step of detecting said one or more detectable signals resulting from said scattering or diffraction of energy;

are both carried out using a scanning electron microscope.

149. The process for treating a material of claim 139 wherein said one or more detectable signals result from absorption of said energy by at least one of said one or more semiconductor nanocrystals.

150. The process for treating a material of claim 139 wherein said one or more semiconductor nanocrystals in said one or more probes are capable of providing said one or more detectable signals as electromagnetic radiation emitted by said one or more semiconductor nanocrystals.

151. The process for treating a material of claim 150 wherein said one or more semiconductor nanocrystals are capable of emitting electromagnetic radiation in a narrow wavelength band when exposed to said energy.

152. The process for treating a material of claim 150 wherein said electromagnetic radiation emitted by said one or more semiconductor nanocrystals comprises visible light.

153. The process for treating a material of claim 150 wherein said electromagnetic radiation emitted by said one or more semiconductor nanocrystals comprises ultraviolet light.

154. The process for treating a material of claim 150 wherein said electromagnetic radiation emitted by said one or more semiconductor nanocrystals comprises infrared light.

155. The process for treating a material of claim 139 wherein said energy to which said one or more semiconductor nanocrystals are exposed comprises electromagnetic radiation of a broad wavelength band; and said one or more detectable signals, provided by said one or more semiconductor nanocrystals in response to said exposure, comprise electromagnetic radiation emitted in a narrow wavelength band.

* * * * *

UNITED STATES PATENT AND TRADEMARK OFFICE
CERTIFICATE OF CORRECTION

PATENT NO.    : 6,207,392 B1  
DATED         : March 27, 2001  
INVENTOR(S)   : Shimon Weiss et al.

Page 1 of 1

It is certified that error appears in the above-identified patent and that said Letters Patent is hereby corrected as shown below:

<u>Column 7,</u>  
Line 53, change "5,571,018" to -- 5,751,018 --.  
Line 61, change "5,571,018" to -- 5,751,018 --.

Signed and Sealed this

Twenty-sixth Day of March, 2002

Attest:

JAMES E. ROGAN  
*Attesting Officer*    *Director of the United States Patent and Trademark Office*